(12) United States Patent
Ly et al.

(10) Patent No.: US 12,025,788 B2
(45) Date of Patent: Jul. 2, 2024

(54) SYSTEM AND METHOD FOR SIMULTANEOUS LONGITUDINAL BIOLOGICAL IMAGING

(71) Applicant: The Regents of the University of California, Oakland, CA (US)

(72) Inventors: Victoria Ly, Santa Cruz, CA (US); Pierre Baudin, Santa Cruz, CA (US); Yohei Rosen, Santa Cruz, CA (US); Pattawong Pansodtee, Santa Cruz, CA (US); Kateryna Voitiuk, Santa Cruz, CA (US); David Haussler, Santa Cruz, CA (US); Mircea Teodorescu, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 76 days.

(21) Appl. No.: 17/738,239

(22) Filed: May 6, 2022

(65) Prior Publication Data
US 2022/0357566 A1 Nov. 10, 2022

Related U.S. Application Data

(60) Provisional application No. 63/184,913, filed on May 6, 2021, provisional application No. 63/184,915, filed on May 6, 2021, provisional application No. 63/242,449, filed on Sep. 9, 2021.

(51) Int. Cl.
*G02B 21/36* (2006.01)
(52) U.S. Cl.
CPC ......... *G02B 21/367* (2013.01); *G02B 21/365* (2013.01)

(58) Field of Classification Search
CPC ........................... G02B 21/367; G02B 21/365
USPC .......................................................... 348/79
See application file for complete search history.

(56) References Cited

U.S. PATENT DOCUMENTS

| 2012/0194664 A1* | 8/2012 | Kiyota | C12M 41/48 348/79 |
|---|---|---|---|
| 2019/0137753 A1* | 5/2019 | Chan | H04N 23/90 |
| 2020/0017817 A1* | 1/2020 | Kelly-Greene | C12M 41/14 |
| 2020/0339938 A1* | 10/2020 | Bovard | C12M 35/08 |

OTHER PUBLICATIONS

Zhao, H., et al., "A screening platform for glioma growth and invasion using bioluminescence imaging", J. neurosurgery 111, 238-246 (2009).
Almassalha, L. M. et al., "Label-free imaging of the native, living cellular nanoarchitecture using partial-wave spectroscopic microscopy", Proc. Natl. Acad. Sci. 113, E6372-E6381 (2016).
Martin, H. L. et al., "High-content, high-throughput screening for the identification of cytotoxic compounds based on cell morphology and cell proliferation markers", PloS one 9, e88338 (2014).

(Continued)

*Primary Examiner* — Jayanti K Patel
*Assistant Examiner* — Richard B Carter
(74) *Attorney, Agent, or Firm* — Carter, DeLuca & Farrell LLP

(57) ABSTRACT

An imaging device includes an alignment platform configured to hold a cell culture plate having a plurality of wells and an imaging assembly including a plurality of imaging units, each of which is configured to image one well of the plurality of wells.

14 Claims, 15 Drawing Sheets

(56) References Cited

OTHER PUBLICATIONS

Dempsey, G. T. et al., "Cardiotoxicity screening with simultaneous optogenetic pacing, voltage imaging and calcium imaging", J. pharmacological toxicological methods 81, 240-250 (2016).
Honarnejad, K. et al., "Fret-based calcium imaging: a tool for high-throughput/content phenotypic drug screening in alzheimer disease", J. biomolecular screening 18, 1309-1320 (2013).
Park, J., et al., "Estimates of particulate matter inhalation doses during three-dimensional printing: How many particles can penetrate into our body?", Indoor air (2020).
Pearce, J. M., "Building research equipment with free, open-source hardware", Science 337, 1303-1304 (2012).
Mendoza-Gallegos, et al., "An affordable and portable thermocycler for real-time pcr made of 3d-printed parts and off-the-shelf electronics", Anal. chemistry 90, 5563-5568 (2018).
Kwon, H.-S. et al., "Performance of miniper tm mini8, a portable thermal cycler", Anal. Sci. Technol. 29, 79-84 (2016).
Byagathvalli, G., et al., "A 3d-printed hand-powered centrifuge for molecular biology", PLoS biology 17, e3000251 (2019).
González-González, E., et al., "Portable and accurate diagnostics for covid-19: Combined use of the miniper thermocycler and a well-plate reader for sars-cov-2 virus detection", PloS one 15, e0237418 (2020).
Boguraev, A.-S. et al., Successful amplification of dna aboard the international space station:, NPJ microgravity 3, 1-4 (2017).
Hossain, Z. et al., "Interactive and scalable biology cloud experimentation for scientific inquiry and education", Nat. biotechnology 34, 1293-1298 (2016).
Klimaj, S. D., et al., "A high-throughput imaging and quantification pipeline for the evos imaging platform", Plos one 15, e0236397 (2020).
Ruckdäschel, S., "Time lapse imaging of spheroids-zencellowl incubator microscope", OMNI Life Sci. (2017).
Early, J. J. et al., "An automated high-resolution in vivo screen in zebrafish to identify chemical regulators of myelination", Elife 7, e35136 (2018).
Tsuji, N. et al., "Whole organism high content screening identifies stimulators of pancreatic beta-cell proliferation", PloS one 9, e104112 (2014).
Lemieux, G. A. et al., A whole-organism screen identifies new regulators of fat storage, Nat. chemical biology 7, 206-213 (2011).
Schreiber, K., et al., "A high-throughput chemical screen for resistance to pseudomonas syringae in *Arabidopsis*", The Plant J. 54, 522-531 (2008).
Renner, H. et al., "A fully automated high-throughput workflow for 3d-based chemical screening in human midbrain organoids", Elife 9, e52904 (2020).
Schuster, B. et al., "Automated microfluidic platform for dynamic and combinatorial drug screening of tumor organoids" Nat. communications 11, 1-12 (2020).
Willsey, H. R. et al., "The neurodevelopmental disorder risk gene dyrka is required for ciliogenesis and control of brain size in xenopus embryos", Development 147 (2020).
Nieuwkoop, P. D. & Faber, J., "Normal table of xenopus laevis (daudin)", Copeia 1958, 65-65 (1958).
Thomson, J. A. et al., "Embryonic stem cell lines derived from human blastocysts", science 282, 1145-1147 (1998).
Specht, E. A., et al., "A critical and comparative review of fluorescent tools for live-cell imaging", Annu. review physiology 79, 93-117 (2017).
Godin, A. G., et al., "Super-resolution microscopy approaches for live cell imaging", Biophys. Journal 107, 1777-1784 (2014).
Miller, A. R. et al., "Portable, battery-operated, low-cost, bright field and fluorescence microscope", PloS one 5, e11890 (2010).
Selinummi, J. et al., "Bright field microscopy as an alternative to whole cell fluorescence in automated analysis of macrophage images", PloS one 4, e7497 (2009).
Hernández Vera, R., et al., "A modular and affordable time-lapse imaging and incubation system based on 3d-printed parts, a smartphone, and off-the-shelf electronics", PLoS One 11, e0167583 (2016).
Savas, J., et al., "Toward fully three-dimensional-printed miniaturized confocal imager", Opt. Eng. 57, 041402 (2018).
Wincott, M. B. et al. "Democratising "microscopi": a 3d printed automated XYZT fluorescence imaging system for teaching, outreach and fieldwork", bioRxiv (2020).
Yao, S., et al., "Automatic three-dimensional imaging for blastomere identification in early-stage embryos based on brightfield microscopy", Opt. Lasers Eng. 130, 106093 (2020).
Zamxaka, M., et al., "Microbiological and physico-chemical assessment of the quality of domestic water sources in selected rural communities of the eastern cape province, south africa", Water Sa 30, 333-340 (2004).
Ferreira, L. M. et al. "Effective participatory science education in a diverse latin american population", Palgrave Commun. 5, 63 (2019).
Giacomotto, J. & Ségalat, L. "High-throughput screening and small animal models, where are we?", Br. journal pharmacology 160, 204-216 (2010).
Willis, S., "The maker revolution", Computer 51, 62-65 (2018).
Barber, K. & Mostajo-Radji, "M. A. Youth networks' advances toward the sustainable development goals during the covid-19 pandemic", Front. Sociol. 5: 589539. doi: 10.3389/fsoc (2020).
Coakley, M. F. et al., "The nih 3d print exchange: a public resource for bioscientific and biomedical 3d prints", 3D printing additive manufacturing 1, 137-140 (2014).
Ambrose, B. et al., "Democratizing single-molecule fret: An open-source microscope for measuring precise distances and biomolecular dynamics", Biophys. J. 118, 614a (2020).
Gross, B. C., et al., "Evaluation of 3d printing and its potential impact on biotechnology and the chemical sciences", ACS Publ. (2014).
Baden, T. et al., "Open labware: 3-d printing your own lab equipment", PLoS biology 13, e1002086 (2015).
Alessandri, K. et al., "All-in-one 3d printed microscopy chamber for multidimensional imaging, the universlide", Sci. reports 7, 1-10 (2017).
Ventola, C. L., "Medical applications for 3d printing: current and projected uses", Pharm. Ther. 39, 704 (2014).
Beattie, R. J., et al., "Sparking curiosity through open-source platforms in education and science. Front", Educ. 5, 8 (2020).
Brown, J. W. et al., "Single-molecule detection on a portable 3d-printed microscope", Nat. communications 10, 1-7 (2019).
Khan, A., et al., "A low-cost 3d printed microfluidic bioreactor and imaging chamber for live-organoid imaging", Biomicrofluidics (2021).
Chagas, A. M., et al., "TheC 100 lab: A 3d-printable open-source platform for fluorescence microscopy, optogenetics, and accurate temperature control during behaviour of zebrafish, *Drosophila*, and caenorhabditis elegans", PLoS biology 15, e2002702 (2017).
Kim, S. B. et al., "A mini-microscope for in situ monitoring of cells", Lab on a Chip 12, 3976-3982 (2012).
Diederich, B. et al., "A versatile and customizable low-cost 3d-printed open standard for microscopic imaging", Nat. communications 11, 1-9 (2020).
Wang, Z. et al., "A high-resolution minimicroscope system for wireless real-time monitoring", IEEE Transactions on Biomed. Eng. 65, 1524-1531 (2017).
Zhang, Y. S. et al., "A cost-effective fluorescence mini-microscope for biomedical applications", Lab on a Chip 15, 3661-3669 (2015).
Zhang, C., et al., "Open-source 3d-printable optics equipment", PloS one 8, e59840 (2013).
Collins, J. T. et al., "Robotic microscopy for everyone: the openflexure microscope", Biomed. Opt. Express 11, 2447-2460 (2020).
Cybulski, J. S., et al., "Foldscope: origami-based paper microscope", PloS one 9, e98781 (2014).
Kim, H. et al., "Ludusscope: accessible interactive smartphone microscopy for life-science education", PloS one 11, e0162602 (2016).
Aidukas, T., et al., "Low-cost, sub-micron resolution, wide-field computational microscopy using opensource hardware", Sci. reports 9, 1-12 (2019).

(56) References Cited

OTHER PUBLICATIONS

Bohm, A., "An inexpensive system for imaging the contents of multi-well plates", Acta Crystallogr. Sect. F: Struct. Biol. Commun. 74, 797-802 (2018).

Merces, G. O. et al., "The incubot: A 3d printer-based microscope for long-term live cell imaging within a tissue culture incubator", BioRxiv (2020).

Gürkan, G.& Gürkan, K., "Incu-stream 1.0: an open-hardware live-cell imaging system based on inverted bright-field microscopy and automated mechanical scanning for real-time and long-term imaging of microplates in incubator", IEEE Access 7, 58764-58779 (2019).

Kim, J., Henley, et al., "Incubator embedded cell culture imaging system (emsight) based on fourier ptychographic microscopy", Biomed. optics express 7, 3097-3110 (2016).

Uno, A. Arduino uno. online, (https://store.arduino.cc/usa/arduino-uno-rev3, diakses) 4 (2019).

Pi, R. Raspberry pi 4. online.(https://www.raspberrypi.org) (2015).

Beam, M. Makerbeam 10mmx10mm. online].(https://www.makerbeam.com/makerbeam/ (2021).

Fruit, A. Zero spy camera for raspberry pi zero. online.(https://www.adafruit.com/product/3508) (2015).

Goda, T. et al., "Genetic screens for mutations affecting development of xenopus tropicalis", PLoS Genet. 2, e91 (2006).

Borodinsky, L. N., "Xenopus laevis as a model organism for the study of spinal cord formation, development, function and regeneration", Front. neural circuits 11, 90 (2017).

Olmstead, A. W. et al., "Reproductive maturation of the tropical clawed frog: *Xenopus tropicalis*", Gen. comparative endocrinology 160, 117-123 (2009).

Hirsch, N., et al., "Xenopus, the next generation: X. tropicalis genetics and genomics", Dev. dynamics: an official publication Am. Assoc. Anat. 225, 422-433 (2002).

Mcnamara, S., et al., "Husbandry, general care, and transportation of xenopus laevis and xenopus tropicalis", Methods Mol Biol., 1-17 (Springer, 2018).

Khokha, M. K. et al., "Techniques and probes for the study of xenopus tropicalis development", Dev. dynamics: an official publication Am. Assoc. Anat. 225, 499-510 (2002).

Keller, R. & Sutherland, A., "Convergent extension in the amphibian, *Xenopus laevis*", In Current topics in developmental biology, vol. 136, 271-317 (Elsevier, 2020).

Baldwin, A., Kim, J. & Wallingford, J. B., "Global analysis of cell behavior and protein localization dynamics reveals region-specific functions for shroom3 and n-cadherin during neural tube closure", bioRxiv (2021).

Huebner, R. J. et al., "Cadherin clustering controls heterogeneous, asymmetric junction dynamics during vertebrate axis elongation", bioRxiv (2020).

Abe-Fukasawa, N., et al., "Novel 3d liquid cell culture method for anchorageindependent cell growth, cell imaging and automated drug screening", Sci. reports 8, 1-12 (2018).

\* cited by examiner

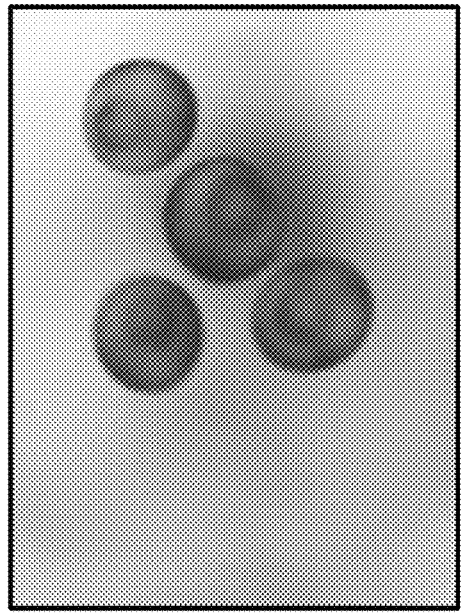
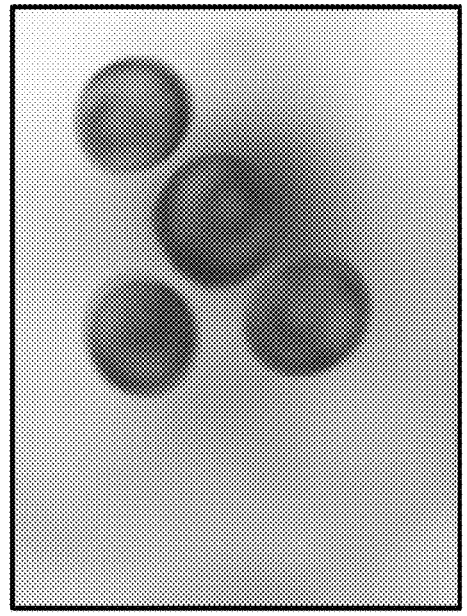
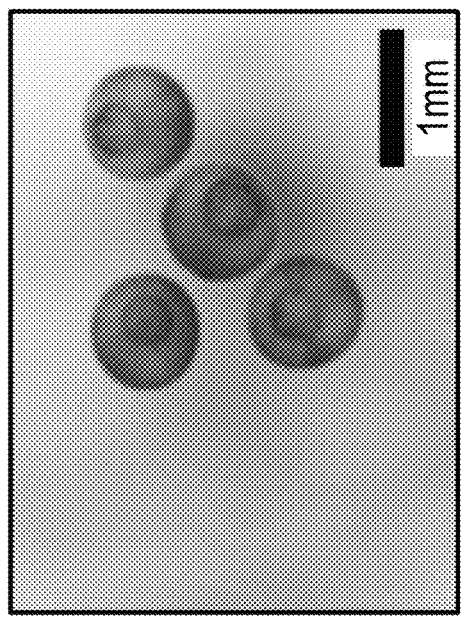
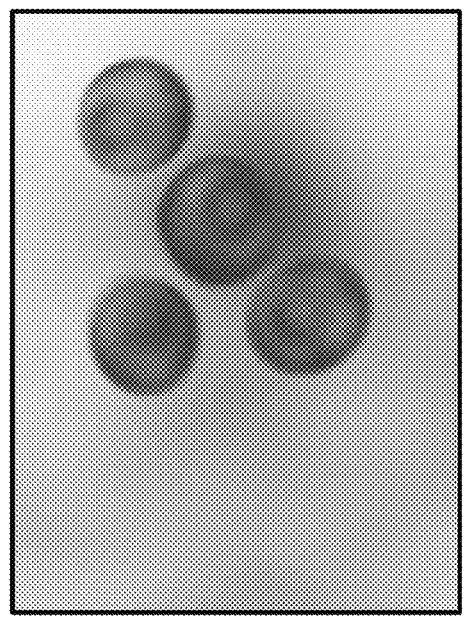
FIG. 11

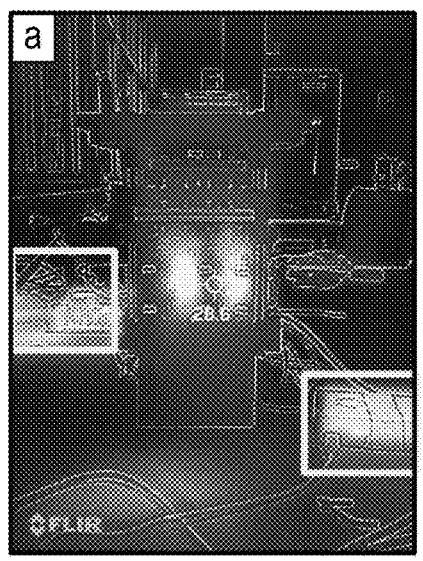
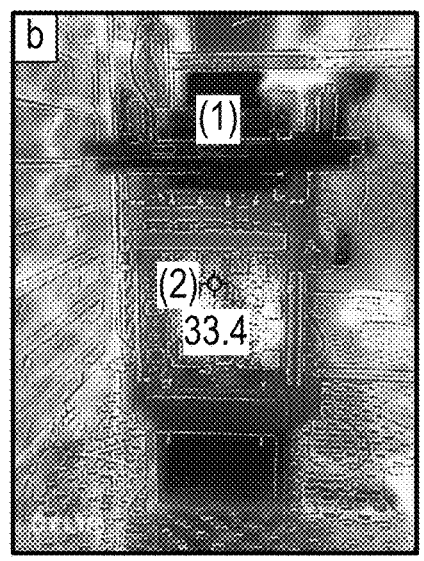
FIG. 16A    FIG. 16B
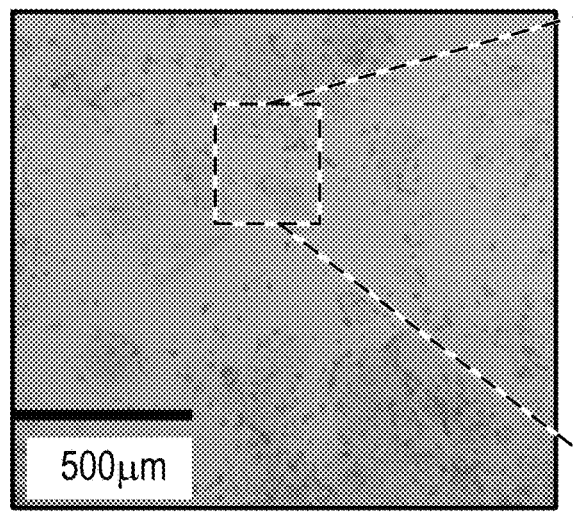
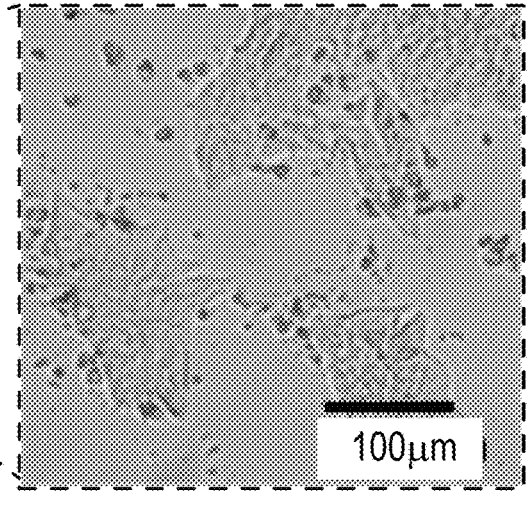
FIG. 17
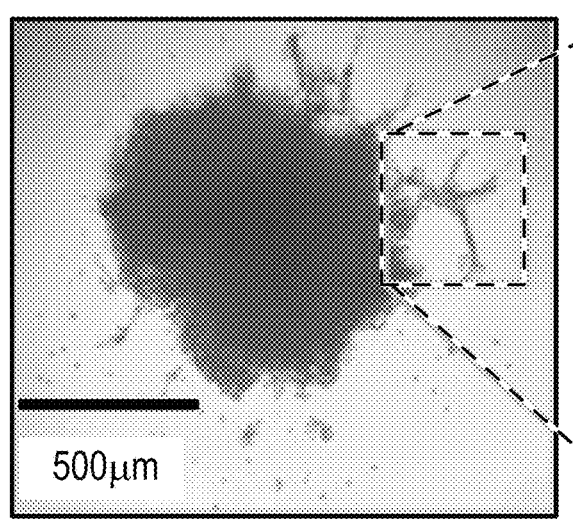
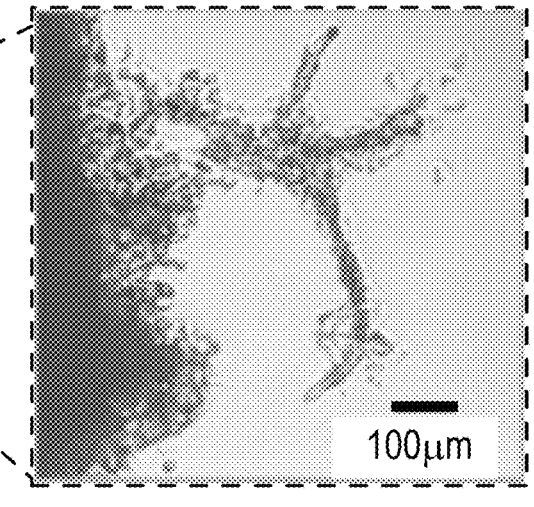
FIG. 18

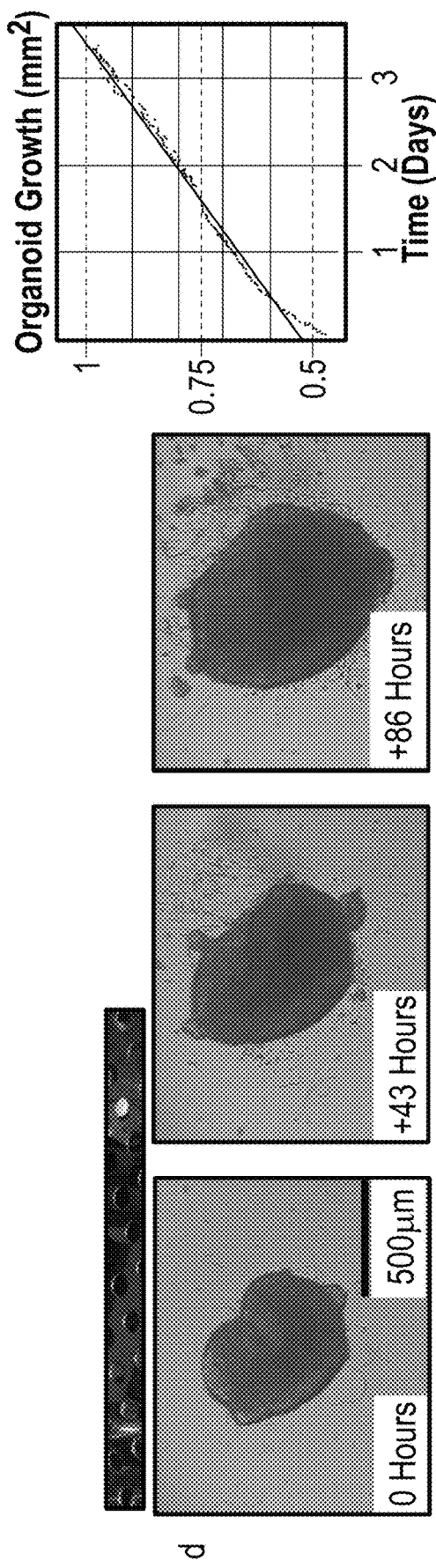
FIG. 19A
FIG. 19B
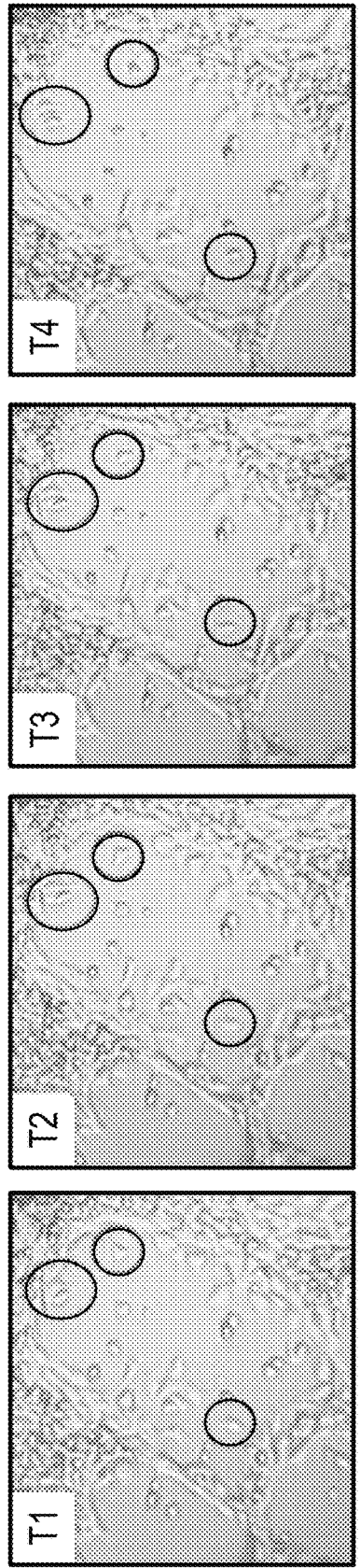
FIG. 20

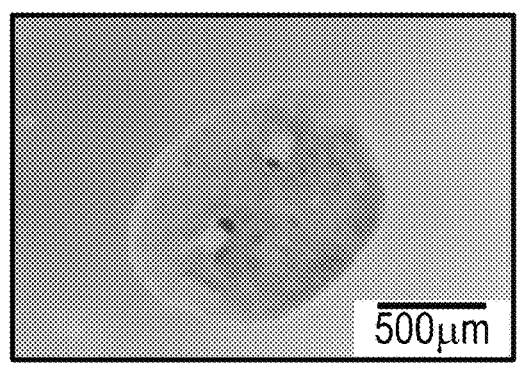
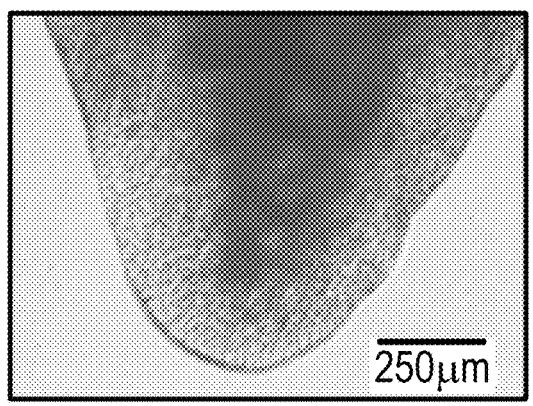
FIG. 21
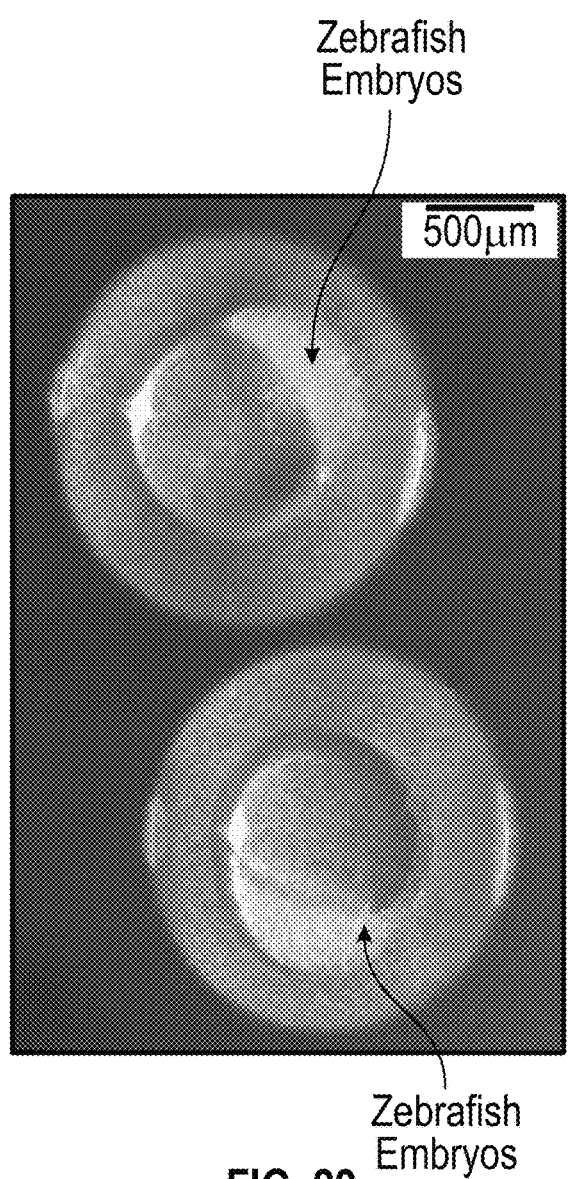
Zebrafish Embryos
Zebrafish Embryos
FIG. 22
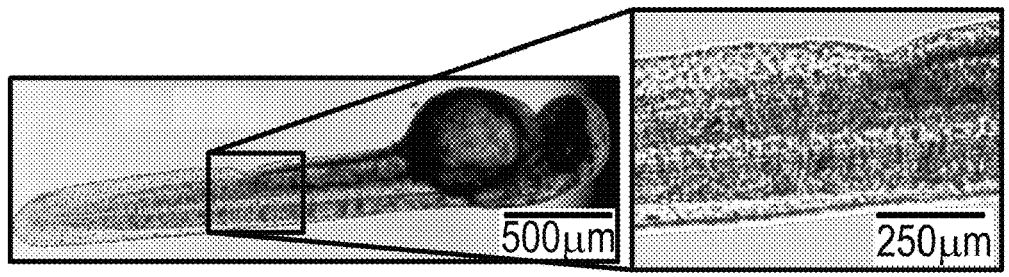
FIG. 23

SYSTEM AND METHOD FOR SIMULTANEOUS LONGITUDINAL BIOLOGICAL IMAGING

CROSS-REFERENCE TO RELATED APPLICATION

The present application claims the benefit of and priority to U.S. Provisional Application No. 63/184,913, filed on May 6, 2021; U.S. Provisional Application No. 63/184,915, filed on May 6, 2021; and U.S. Provisional Application No. 63/242,449, filed on Sep. 9, 2021. The entire disclosures of each of the foregoing applications are incorporated by reference herein.

GOVERNMENT LICENSE RIGHTS

This invention was made with government support under the National Institute of Mental Health of the National Institutes of Health under Award No. R01MH120295, the National Science Foundation under Award No. NSF 2034037, and the National Human Genome Research Institute under Grant No. T32HG008345. The Government has certain rights in the invention.

BACKGROUND

Monitoring and handling live tissues and cell cultures as well as analyzing their secreted contents are essential tasks in experimental biology and biomedicine. Advances in microscopy have revolutionized biological studies, allowing scientists to perform observations of cellular processes and organisms' development and behaviors. Imaging has been pivotal to uncovering cellular mechanisms behind biological processes.

Longitudinal studies involve repeated observations, i.e., imaging, of samples over a desired period of time. Several options exist for performing longitudinal imaging of biological materials. These range from super-resolution microscopes that allow for imaging of individual biomolecules to conventional benchtop microscopes, which are common in academic research, industrial, and teaching laboratories.

When choosing between the different technologies for longitudinal live tissue imaging, several factors may be considered in the experimental design. These include the speed of the microscope being sufficient for the phenomenon being studied as well as microscope's ability to acquire images without damaging or disturbing the specimen, e.g., photobleaching. Additional factors include microscope's ability to image in the environmental conditions of the desired experiment, including temperature, light, and humidity. Furthermore, it is important that the resolution of the microscope is sufficient to view the phenomenon being studied. Conventional devices that are capable of simultaneous multi-well longitudinal tissue imaging are bulky and/or expensive. Thus, there is a need for an imaging device capable of meeting all of the above criteria while being affordable and having a smaller-footprint than conventional imaging devices.

SUMMARY

The use of open-source technology, including 3D printers, laser cutters, and low-cost computer hardware, has democratized access to rapid prototyping tools and dramatically increased the repertoire of biomedical equipment available to laboratories around the world. Through rapid prototyping and the use of open-source platforms, technology can be replicated and quickly improved.

Typically, 3D manufacturing has two main approaches: additive (e.g., 3D printing) and subtractive (e.g., machining, laser cutting), with both methods requiring dedicated equipment. In the past some of these devices were limited to specialized manufacturing facilities. Over the past couple of decades, 3D manufacturing went through a revolution. Equipment such as 3D printers and computer numerical control (CNC) machinery has become affordable and ubiquitous in engineering laboratories. Research in the areas of labs-on-chip, optofluidics, microscopy, in combination with developments in consumer-oriented tools for makers, has the potential to democratize access to cell biology-based research. Laboratories are now able to more easily develop custom devices which can be shared with the greater research community as open-source projects. The present disclosure provides for an imaging device that takes advantage of these developments.

3D printer technology has been applied to several fields in biomedicine, including biotechnology bioengineering, and medical applications including fabrication of tissues and organs, casts, implants, and prostheses. Existing 3D printed microscopes range in complexity from simple low-cost systems with pre-loaded imaging modules to portable confocal microscopes capable of imaging individual molecules and even 3D printed microfluidic bioreactors. The majority of low-cost 3D printed microscopes are not intended for longitudinal imaging of simultaneous biological cultures (e.g., multi-well, multi-week biological experiments). They usually have a single imaging unit or perform confocal, and even light-sheet imaging. Other systems utilize a single camera attached to a gantry system to perform imaging of multiple experimental replicates. Few 3D-printed microscopes have been developed that perform multi-well imaging with medium throughput. Several biological applications would greatly benefit from multi-well, multi-week simultaneous imaging. These include cell culture applications, in which 2D and 3D culture models can be tracked over multi-week periods, as well as developmental and behavioral biology experiments in which multi-week tracking could be performed on whole organisms.

Simultaneous imaging of biological systems is crucial for drug discovery, genetic screening, and high-throughput phenotyping of biological processes and disease. This technique typically requires expensive multicamera and robotic equipment, making it inaccessible to most laboratories. While the need for a low-cost solution has long been appreciated, few such solutions have been proposed. Currently, the low-cost solutions can be grouped in two categories: 1) those that use of gantry systems that move an individual camera through multiple wells, performing "semi-simultaneous" imaging or 2) those that use acquisition of large fields of view encompassing multiple wells, which results in limited resolution per well, followed by post-processing images. Neither of these solutions is optimal to perform true simultaneous imaging of biological replicates across multiple conditions. To overcome these limitations, the imaging device according to the present disclosure is configured to perform an automated image capture of a standard 24 wells cell culture plate (also known as a tissue culture plate) using 24 individual objectives.

Commercial electronic systems for simultaneous imaging of biological samples are typically designed to image cells plated in monolayers. Yet, significant attention has been paid to longitudinal imaging-based screens using whole organisms. These have included zebrafish, worms, and plants.

Many times, the results of the screens are based on single plane images or in maximal projections obtained from external microscopes. The imaging device according to the present disclosure overcomes these limitations and can image along the z-axis. This is accomplished with fine adjustment by stepper motors that lift an elevator platform that holds all of the imaging units, each having an objective lens and a camera.

To date, few 3D printed microscopes are designed to function inside incubators. The presently disclosed imaging device may operate inside an incubator for up to 4 weeks. This allows the imaging device to operate with screens in 3D mammalian models including organoids. Since the imaging device according to the present disclosure may be used inside incubators, the imaging device may be used to perform longitudinal imaging of human cortical organoids and analyzing the behavior and movement of individual cells and other mammalian tissue at optimal growth temperatures of about 37° C.

Simultaneous longitudinal imaging across multiple conditions and replicates has been crucial for scientific studies aiming to understand biological processes and disease. Yet, imaging devices capable of accomplishing these tasks are economically unattainable for most academic and teaching laboratories around the world. The present disclosure provides a low-cost imaging device with a current per-well cost of less than $100 for simultaneous longitudinal biological imaging made primarily using off-the-shelf and 3D-printed materials.

The imaging device according to the present disclosure provides simultaneous multi-well imaging and may perform longitudinal brightfield z-stack imaging of the wells of any suitable cell culture plate, including conventional 24-well cell culture plates. The imaging device is also configured to capture 3D z-stack image data. The imaging device is configured to capture stacks of images and/or video at different focal layers, which is referred to as "z-plane stack" or "z-stack" due to the focal planes being stacked along a vertical, or z-axis. The imaging device is configured to simultaneously images in each one of a plurality (e.g., 24) of wells at multiple focal planes (the resolution of the "z-stack" can be remotely modified) at any suitable frequency, which may be impractical to perform manually. The imaging frequency may be from about 1 minute to about 24 hours, and images may be taken for any suitable period of time, which may be from 1 hour to about 30 weeks.

The disclosed imaging device is designed to illuminate the samples using one or more lighting sources from above and/or below the cell culture plate. Diffused illumination from below results in images that show contours and surface features. Illumination from above results in more visible detail and can show internal structures if the sample is sufficiently translucent. The flexibility of using different illumination techniques emulates commercial brightfield microscopes. The imaging device also includes an alignment platform which supports a cell culture plate containing biological samples during an experiment. The alignment platform may be moved along two axes (e.g., x axis and y axis) defining a horizontal plane.

The imaging device further includes a plurality of imaging units, which may correspond to the number of cells of the cell culture plate, e.g., 24. The imaging units are coupled to an elevator platform configured to move along one or more support columns. One or more stepper motors are configured to move the elevator platform vertically along a vertical axis (i.e., the z axis) transverse to the horizontal plane of the alignment platform. The stepper motors may have a travel per step rate of from about 1 μm to about 10 μm to allow for focusing of specific biological features and collecting z-stack imaging. The imaging device may be controlled remotely via a remote computer, allowing for automatic imaging with minimal intervention from the investigator. Images are uploaded to the remote computer or server as they are captured allowing the user to view the results in near real time.

Examples of using the imaging device according to the present disclosure are also provided and include longitudinal imaging of whole organisms to longitudinally track different animal models of development and regeneration, including *Xenopus tropicalis* (frogs), *Danio rerio* (zebrafish), and *Dugesia tigrina* (planaria worms). Other examples include imaging human embryonic stem cells and 3D cortical organoids inside a standard tissue culture incubator to observe 2D monolayers and 3D mammalian tissue culture models. The imaging device may be used to monitor and measure the behavior of entire organisms or individual cells over any period of time.

Many useful applications of the imaging device and versions thereof may also be envisioned. While the present disclosure provides exemplary uses of the imaging device disclosed herein, the versatility of the imaging device may be employed across various animal and cell models in different environmental conditions. The modular nature of the system allows for new features to be easily built and added, such as defined spectrum LED light sources and filters for fluorescent imaging may be added to enable longitudinal studies of the appearance and fate of defined sub populations of cells in a complex culture by taking advantage of genetically encoded fluorescent reporter proteins. Similarly, the use of fluorescent reporters or dyes that respond to dynamic cell states such as calcium sensors allow long-term imaging of cell activity. The imaging device disclosed herein provides increased accessibility and democratization of multi-well, multi-week simultaneous imaging experiments in diverse biological systems.

According to one embodiment of the present disclosure, an imaging device is disclosed. The imaging device includes an alignment platform configured to hold a cell culture plate having a plurality of wells and an imaging assembly including a plurality of imaging units, each of which is configured to image one well of the plurality of wells.

Implementations of the above embodiment may include one or more of the following features. According to one aspect of the above embodiment, the imaging device may also include an elevator platform configured to support the imaging assembly and to move along a vertical axis transverse to a plane defined by the alignment platform. The imaging device may further include a base and a plurality of columns extending vertically therefrom. The elevator platform may be slidably coupled to the plurality of columns. The imaging device may also include one or more actuators configured to move the elevator platform along the vertical axis. The actuator may be a stepper motor, such as an electric stepper motor. The imaging device may also include a motor controller configured to control the at least one actuator.

Each of the imaging units may include a camera body, a lens, and a camera. The imaging device may also include a controller assembly having a plurality of camera controllers, each of which is coupled to one imaging unit of the plurality of imaging units. The controller assembly may further include one or more interface boards configured to couple to the plurality of camera controllers. The imaging device may include a hub controller configured to communicate with the plurality of camera controllers and the motor controller. The controller assembly, the hub controller, and the motor controller may be coated by a waterproof coating. The alignment platform, the base, and/or the elevator platform may be formed from polylactic acid. The imaging device may be further configured to operate in an incubator at a humidity of from about 75% to about 90% and a temperature of from about 35° C. to about 40° C.

According to another embodiment of the present disclosure, a method for imaging a cell culture plate using an imaging device is disclosed. The method may include moving an imaging assembly of the imaging device relative to an alignment platform, which holds a cell culture plate with a plurality of wells. The imaging assembly is moved along a vertical axis transverse to a plane defined by the alignment platform. The method also includes activating each imaging unit of a plurality of imaging units of the image assembly to obtain an image of each well of a plurality of wells.

Implementations of the above embodiment may include one or more of the following features. According to one aspect of the above embodiment, moving the imaging assembly may include activating at least one actuator configured to move an elevator platform coupled to the imaging assembly. The method may also include operating the imaging device inside an incubator at a humidity of from about 75% to about 90% and a temperature of from about 35° C. to about 40° C. Moving the imaging assembly may include focusing the plurality of imaging units on samples held in the plurality of wells. The method may further include transmitting the images to a remote computer. The method may additionally include processing the images to combine to images to a single image of the cell culture plate.

BRIEF DESCRIPTION OF DRAWINGS

Various embodiments of the present disclosure are described herein below with reference to the figures wherein:

FIG. 11 are images of a sample held in one well taken at four different focal planes 0.3 mm apart using the imaging device according to the present disclosure;

FIG. 16A shows a thermal image of the imaging device of FIG. 1 on a bench top at room temperature of from about 25° C. to about 27° C.;

FIG. 16B shows a thermal image of the imaging device of FIG. 1 inside an incubator from about 35° C. to about 40° C.;

FIG. 17 are images of human embryonic stem cells as a model of 2D-monolayer cell cultures at magnification scales of about 500 μm and 100 μm taken using the imaging device of FIG. 1 according to the present disclosure;

FIG. 18 are images taken using the imaging device of FIG. 1 during longitudinal imaging of human cortical organoids embedded in MATRIGEL® (gelatinous protein mixture available from Corning Life Sciences of Teterboro, NJ) at about 500 μm and 100 μm magnification scales;

FIG. 19A shows images of cortical organoid development over approximately 86 hours taken at 0 hours, 43 hours, and 86 hours using the imaging device of FIG. 1 at a magnification scale of 500 μm;

FIG. 19B shows a plot of size in mm$^2$ of cortical organoid of FIG. 19A over time of about 86 hours;

FIG. 20 are images taken using the imaging device of FIG. 1 during manual longitudinal tracking of migration of individual cells embedded in cortical organoids over approximately 40 minutes with images being taken about every 10 minutes at magnification scales of about 500 μm and 100 μm;

FIG. 21 shows images of regeneration of planaria worms taken using the imaging device of FIG. 1 at magnification scales of about 500 μm and 100 μm;

FIG. 22 is an image of a zebrafish embryo taken at 48 hours post fertilization using the imaging device of FIG. 1 at a magnification scale of 500 μm; and FIG. 23 shows images of a zebrafish embryonic development at an oblong stage taken using the imaging device of FIG. 1 at magnification scales of about 500 μm and 100 μm.

DETAILED DESCRIPTION

Figure 1:
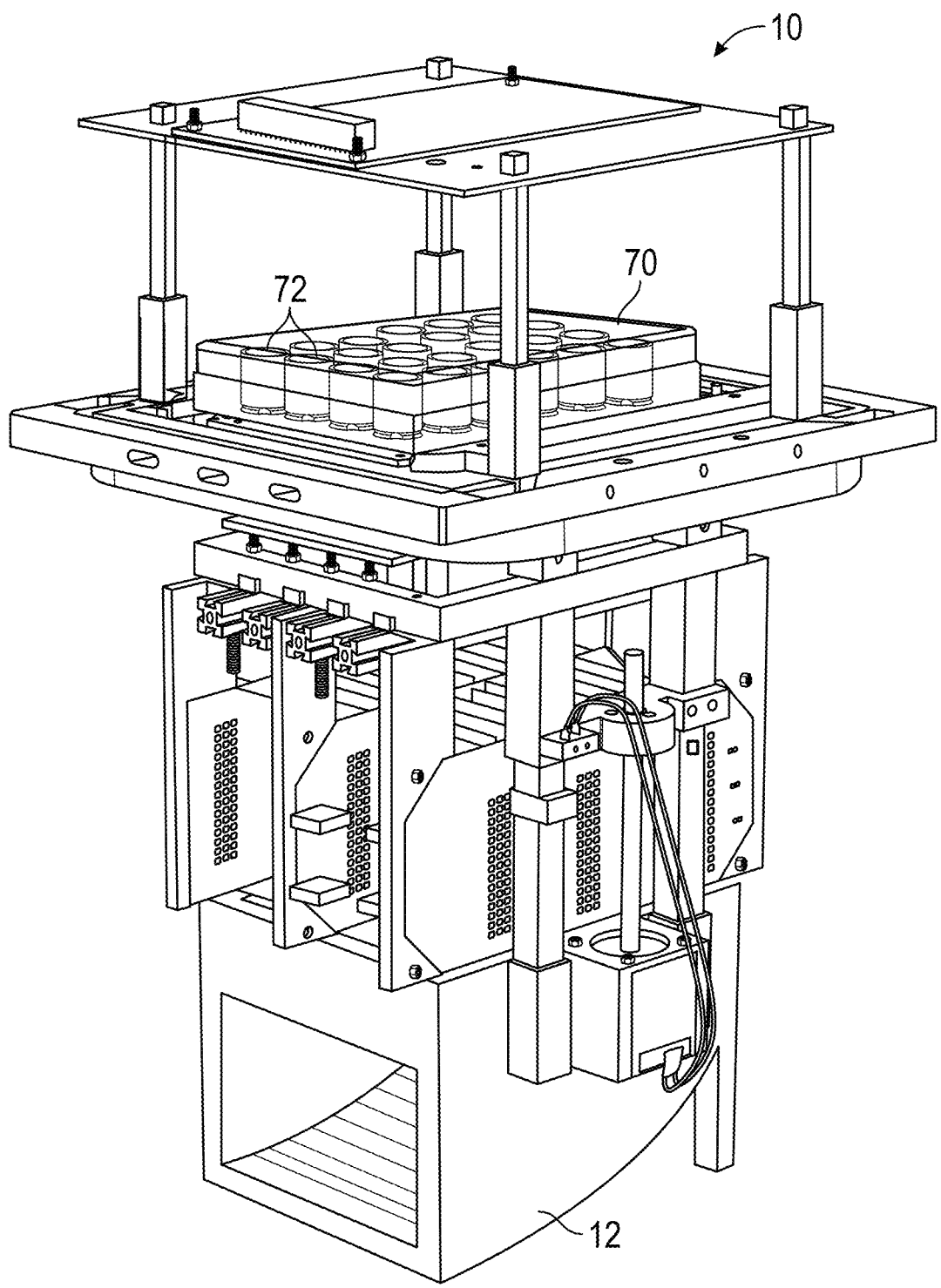
FIG. 1 is a photograph of an imaging device holding a cell culture plate according to one embodiment of the present disclosure.
Figure 2:
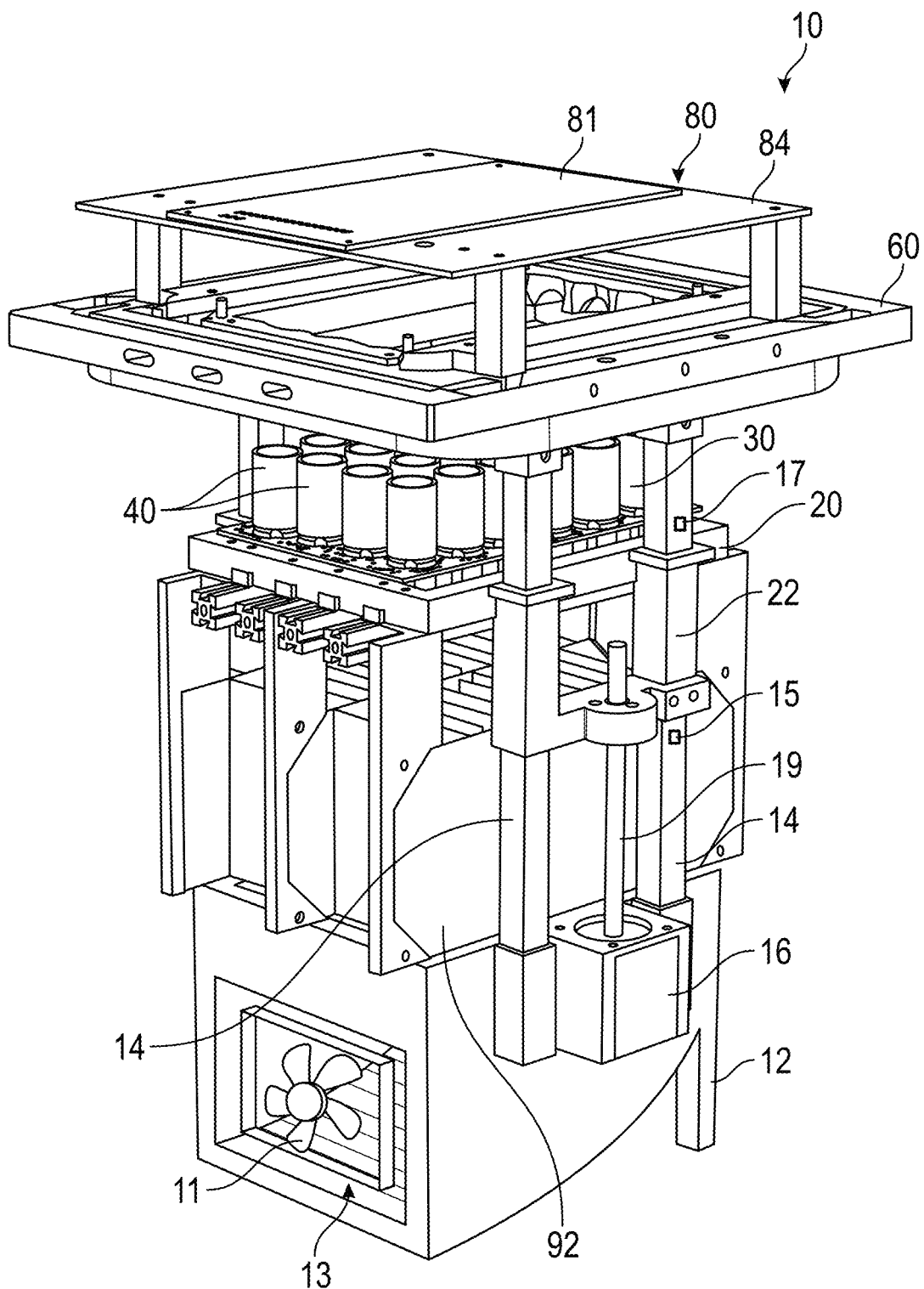
FIG. 2 is a perspective view of the imaging device FIG. 1.

FIGS. 1 and 2 show an imaging device 10 having a base 12 with one or more columns 14 extending vertically from the base 12. The base 12 may include an intake 13 and a fan 11 disposed in communication with the intake 13 for heat dissipation. The base 12 and/or the footprint of the imaging device 10 may be from about 100 cm$^2$ to about 500 cm$^2$ providing for portability of the imaging device 10. In embodiments, the imaging device 10 may have a width and depth of from about 30 cm to about 70 cm and may have a height from about 30 cm to about 80 cm.

The columns 14 may be formed from any suitable rigid material, such as metal. The columns 14 may be formed from aluminum extrusions, such as those available from MakerBeam of Utrecht, Netherlands. The columns 14 may have a square cross-section (e.g., 10 mm×10 mm) and have a length of about 200 mm. The columns 14 are used as guides for an elevator platform 20, which is movable vertically along the columns 14 by one or more actuators 16. The actuators 16 may be electric stepper motors configured to move and hold any discrete position for precisely moving the elevator platform 20. The discrete position, i.e., distance traveled per step, may be from about from about 1 µm to about 10 µm. The elevator platform 20 includes a plurality of sleeves 22, each of which is configured to slidably fit around each of columns 14. Each of the actuators 16 includes a drive shaft 19, which when actuated, moves the elevator platform 20 along a vertical axis. Various mechanical interfaces that convert rotational motion output by the actuators 16 and/or the drive shaft 19 into linear motion of the elevator platform 20 may be used, and include, but are not limited to, worm gears, bevel gears, and the like. Mechanical interfaces may be disposed at the elevator platform 20 and/or the actuators 16.

Figure 3:
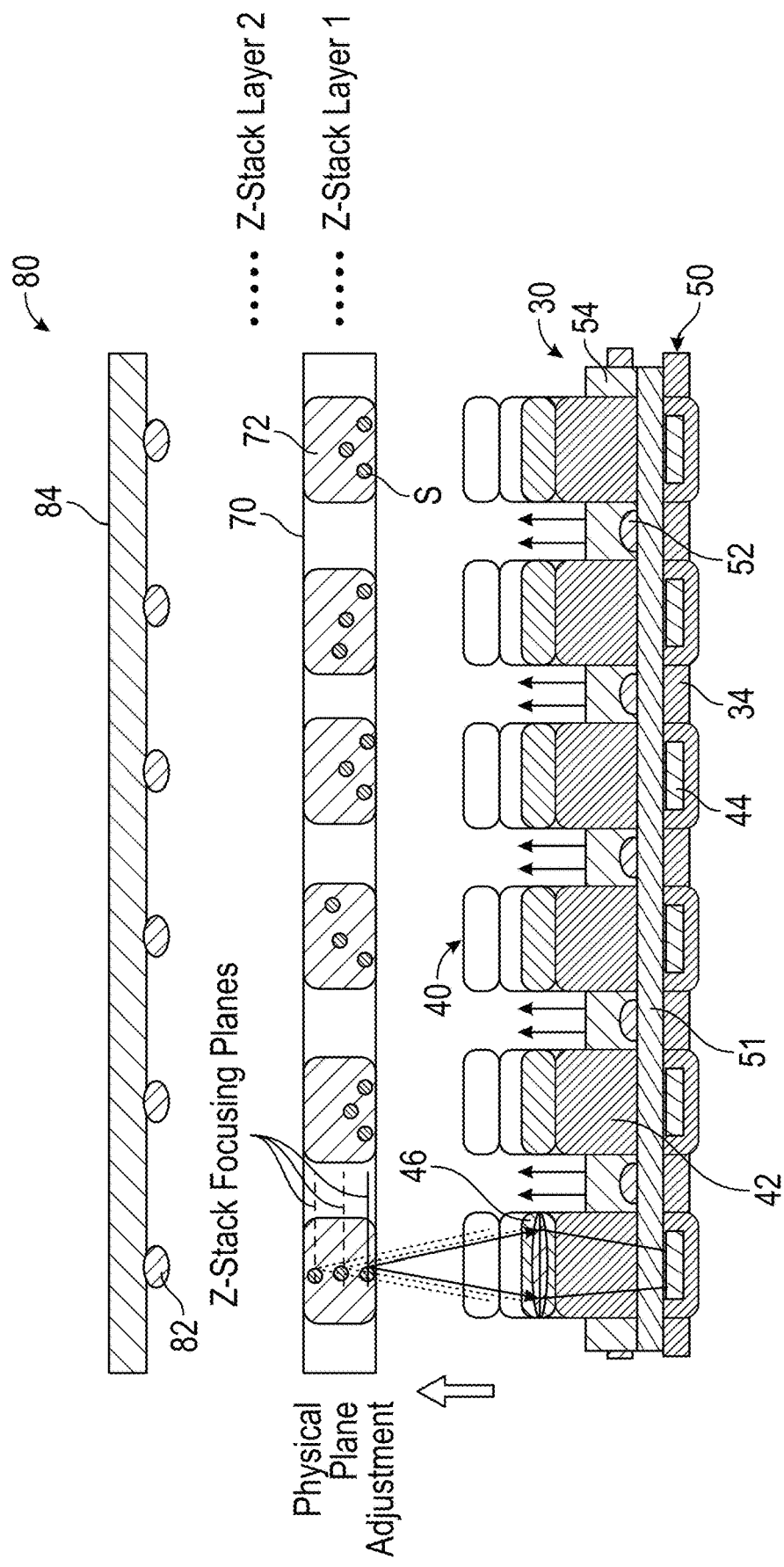
FIG. 3 is a schematic diagram of an array of imaging assemblies and the cell culture plate according to one embodiment of the present disclosure.
Figure 4:
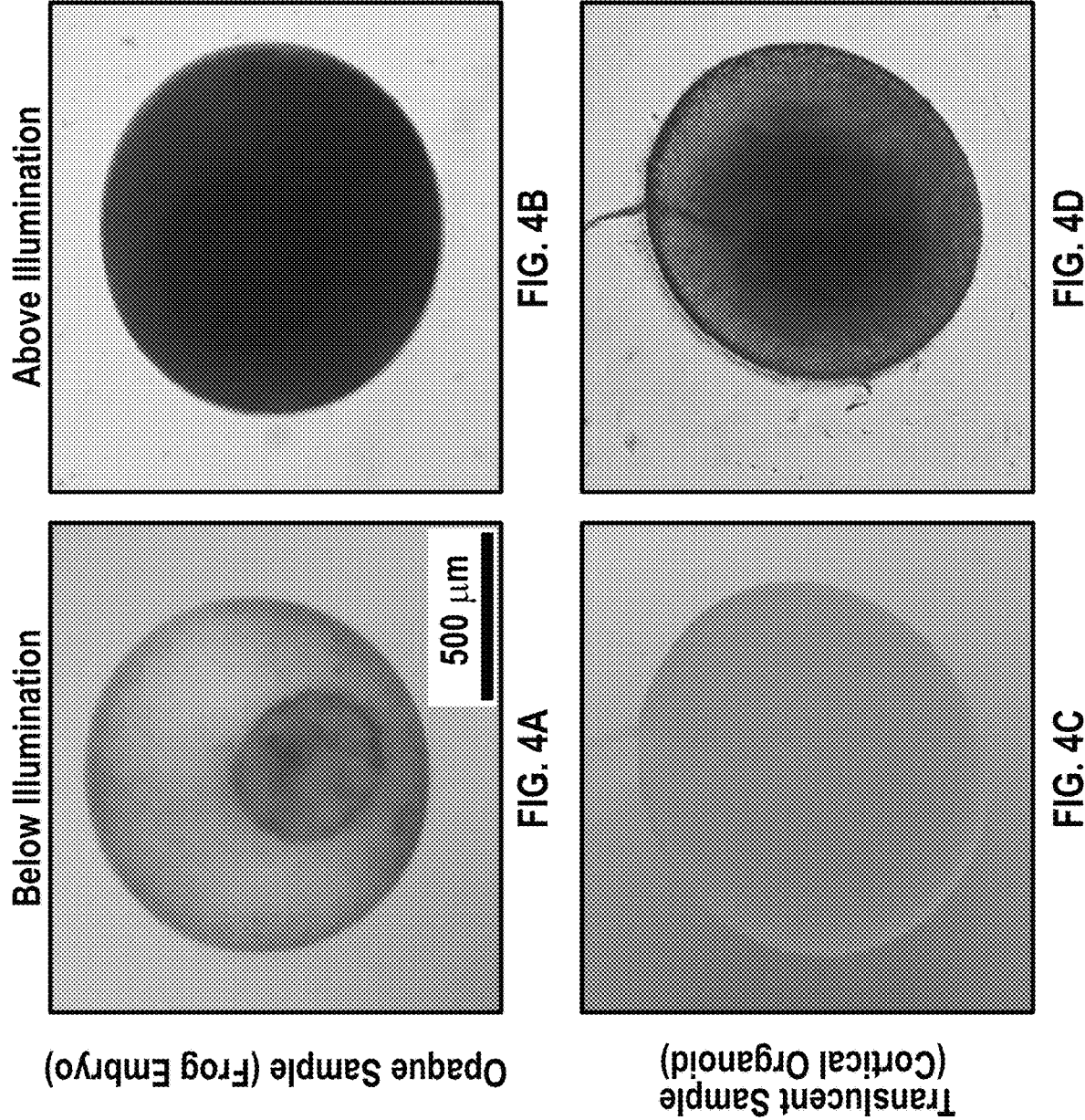
FIGS. 4A and 4B show below (brightfield) and above illuminated images, respectively, of an opaque sample (frog embryo) using the imaging device according to one embodiment of the present disclosure.
FIGS. 4C and D show below (brightfield) and above illuminated images, respectively, of a translucent sample (cortical organoid) using the imaging device according to one embodiment of the present disclosure.
Figure 5:
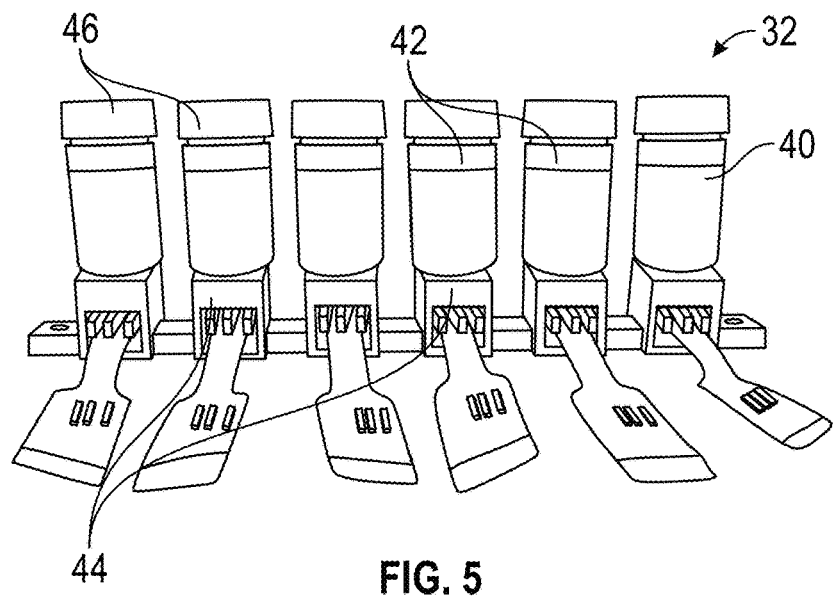
FIG. 5 is a side view of the array of imaging assemblies according to one embodiment of the present disclosure.
Figure 6:
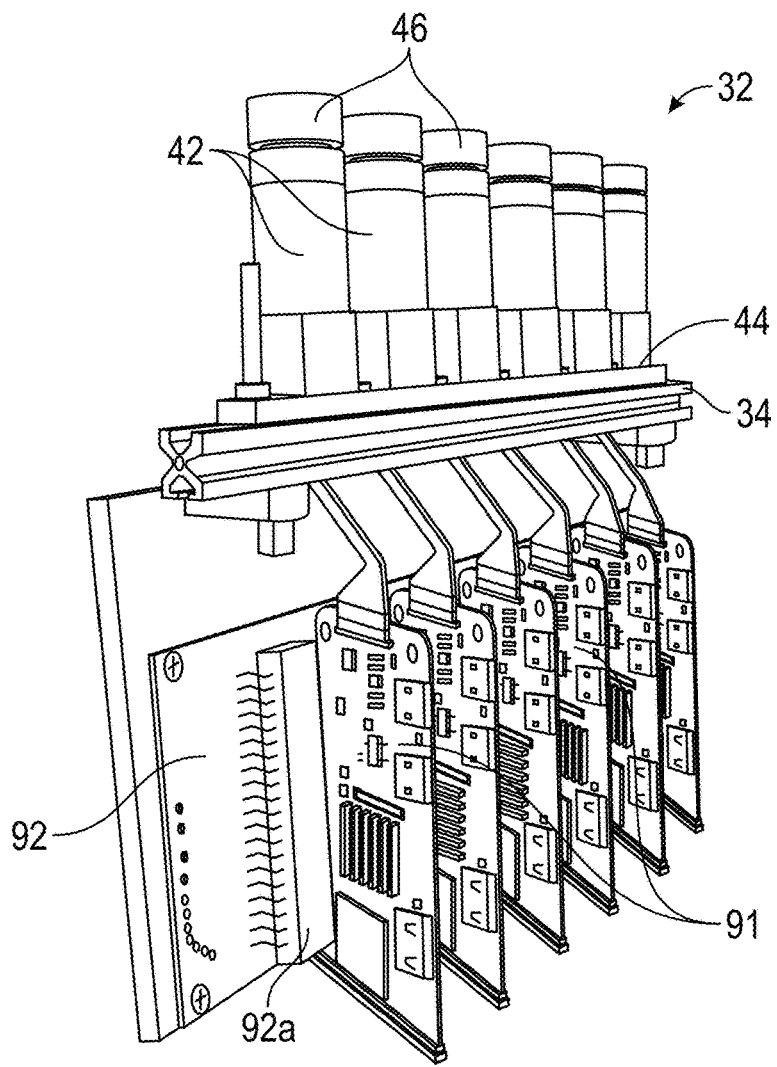
FIG. 6 is a perspective view of the array of imaging assemblies and camera controllers according to one embodiment of the present disclosure.

The elevator platform 20 supports an imaging assembly 30 having a plurality of imaging units 40 disposed in a matrix, i.e., a plurality of imaging arrays of imaging units 40. With reference to FIGS. 3, 5, and 6, an imaging array 32 is shown having a plurality of imaging units 40. Each imaging array 32 may have any suitable number of imaging units 40, which may be from 1 to 10, depending on the number of cells being imaged. The imaging array 32 includes a support 34 for securing the imaging units 40. The support may be an aluminum rod have a square cross-section (e.g., 10 mm×10 mm) having a length of about 150 mm.

Each of the imaging units 40 includes a camera body 42 housing a camera 44 and a lens assembly 46. The camera 44 may be any digital image capturing device, such as Raspberry Pi Camera Module v2, and may have any suitable resolution, e.g., 5 MP and pixel pitch of about 1.4 µm×1.4 µm. The lens assembly 46 may have an optical format of 1/2.5" and a focal length of 16 mm, such as Arducam 1/2.5" M12 mount 16 mm focal length camera lens. The lens assembly 46 may have any number of lenses and may have any desired focal length for imaging the samples "S".

The imaging assembly 30 also includes a first illumination assembly 50 having a substrate 51, which may be a printed circuit board (PCB) or any other suitable rigid substrate. The PCB may be a 1.6 mm FR4 two-layer PCB. The first illumination assembly 50 includes a plurality of light emitting devices 52, which may be light emitting diodes (LEDs) or the like. The LEDs 52 are disposed on the substrate 51 and are located between the imaging units 40 allowing for forward lighting of the samples "S". The first illumination assembly 50 also includes a light diffusing layer 54, which may be formed from any suitable transparent material, such as acrylics, and the like. The light diffusing layer 54 may be used to encase the LEDs 52 on the substrate 51. The light diffusing layer 54 may be machined from a sheet of acrylic, which may have a thickness from about 5 mm to about 10 mm, using CNC machines, such as Nomad883 Pro.

With reference to FIGS. 1 and 2, the imaging device 10 also includes an alignment platform 60, which is securely coupled to the columns 14. The alignment platform 60 is configured to support a cell culture plate 70 having a plurality of wells 72. The alignment platform 60 acts as an alignment platform for the cell culture plate 70 relative to the imaging assembly 30. The alignment platform 60 is disposed above the elevator platform 20 such that the imaging assembly 30 is configured to illuminate and image the samples "S" held in the wells 72 of the cell culture plate 70.

Structural components of the imaging device 10 may be formed using any additive techniques, such as 3D printing using MK3S Prusa 3D printer (PRUSA) or any other suitable 3D printer. Polylactic acid (PLA) such as Prusa Slic3r (PRUSA) or any other suitable polymers may be used. In embodiments, other 3D printable materials may be used, such as metals. The parts may be created with computer aided design (CAD) using any suitable application, such as Fusion 360 and AutoCAD (Autodesk). In embodiments, the base 12, the elevator platform 20, the alignment platform 60, and other structural components may be formed using 3D printers. The components may be printed using infill settings from about 80% to about 100% with resolution of about 0.15 mm or higher. In embodiments, supports may be used during printing.

As shown in FIG. 1, the cell culture plate 70 includes 24 wells 72. In embodiments, the cell culture plate 70 may have any number of wells 72, which may be from 4 to 96 wells. The cell culture plate 70 may have any suitable dimensions, including width, length, and height. The wells 72 may also be of any desired dimension, e.g., diameter, depth, and spacing between neighboring wells 72. The design of the imaging device 10 is based on the type of the cell culture plate 70 being used since the number of the imaging units 40, spacing between the imaging units 40, and configuration of the imaging assembly 30 depends on the number, spacing, and configuration of the cell culture plate 70. Thus, in an exemplary embodiment where the cell culture plate 70 includes 24 wells 72, the imaging units 40 are arranged in the same configuration, i.e., in a 4×6 matrix (e.g., 4 rows and 6 columns), such that each of the wells 72 is individually imaged by a corresponding imaging unit 40.

With reference to FIGS. 2 and 3, the imaging device 10 further includes a second illumination assembly 80 disposed above the alignment platform 60. The second illumination assembly 80 is securely coupled to the alignment platform 60. The second illumination assembly 80 is configured to provide backlighting of the samples "S" held in the wells 72 of the cell culture plate 70 and allowing for brightfield imaging. FIGS. 4A-D show below (i.e., brightfield) and above illuminated images of opaque (frog embryo) and translucent (cortical organoid) samples using the first illumination assembly 50 and the second illumination assembly 80.

The second illumination assembly 80 may include a substrate 81 (FIG. 2), which may be a PCB or any other suitable rigid substrate. The second illumination assembly 80 includes a plurality of LEDs 82, which may be light emitting diodes or the like. The LEDs 82 are disposed on the substrate 81 in the same pattern as the imaging units 40 such that each of the LEDs 82, the wells 72, and the imaging units 40 are vertically aligned, i.e., arranged along the same vertical axis. The second illumination assembly 80 also includes a light diffusing layer 84, which may be formed from any suitable transparent material, such as acrylics, and the like. The light diffusing layer 84 may be used to encase the LEDs 82 on the substrate 81.

In embodiments, the LEDs 52 and 82 may output light at any desired wavelength and spectrum. The LEDs 52 and 82 may output white broad-spectrum light. The LEDs 52 and 82 may be MEIHUA white LEDs with a brightness of from about 228 MCD to about 450MCD, and the brightness can be adjusted through a potentiometer. The LEDs 52 and 82 may also be NCD063W3 Chip Light Emitting Diodes.

The LEDs 52 and 82 may be defined spectrum LEDs configured to output infrared or ultraviolet light to enable fluorescent imaging of samples "S". Such light sources may be used to perform longitudinal studies of the appearance and fate of defined sub populations of cells in a complex culture having genetically encoded fluorescent reporter proteins.

Imaging of the samples "S" held within the wells 72 of the cell culture plate 70 occurs by initially adjusting each of the wells 72 to be in alignment with each of the imaging units 40, i.e., along x and y axis. In addition, the vertical distance of the elevator platform 20 is also adjusted, i.e., along the z axis, to focus on a desired z-axis focal plane. This is particularly useful in samples "S" having one or more objects (e.g., embryos) disposed in different vertical (i.e., focal) planes. Transition between different focal planes is accomplished by adjusting the actuators 16 to move the elevator platform 20 by precise amounts, which may be from about 0.1 mm to about 1 mm.

Figure 7:
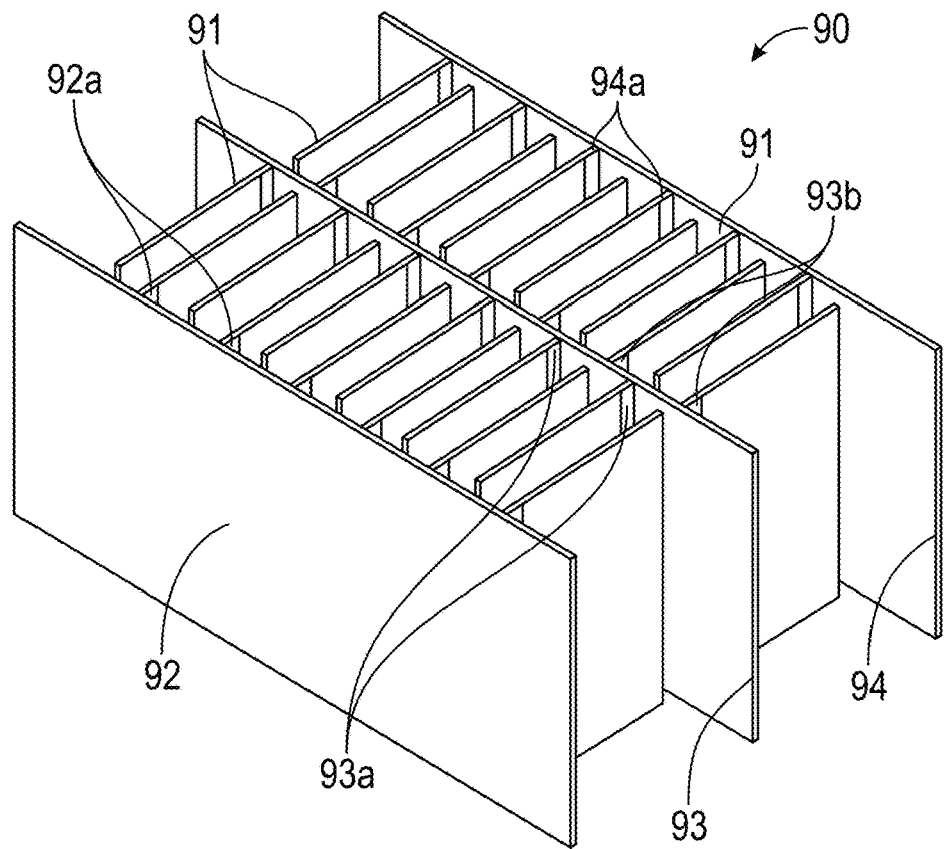
FIG. 7 is a schematic diagram of a controller assembly of the imaging device according to one embodiment of the present disclosure.

With reference to FIGS. 6 and 7, a controller assembly 90 includes a plurality of camera controllers 91, each of which is coupled to one of the cameras 44 using a ribbon cable. The camera controller 91 may be any suitable computing device, such as Raspberry Pi Zero W. As shown in FIGS. 6 and 7, the controller assembly 90 also includes a plurality of interface boards 92, 93, 94 for coupling a plurality of camera controllers 91. Each of the interface boards 92, 93, 94 is a PCB having a plurality of interface connectors 92a, 93a, 93b, 94a, respectively. The interface board 93 is disposed between the interface boards 92 and 94. The connectors 93a are disposed on one side of the interface board 93 facing the interface board 92 while the connectors 93b are disposed on the other side of the interface board 93 facing the interface board 94. Thus, in an arrangement with four rows, three interface boards 92, 93, 94 may be used with the interface boards 92 and 94 each coupling to outside rows of the image units 40 and the middle interface board 93 coupling to two middle rows of the image units. 40. The connectors 93a and 93b are staggered relative to the connectors 92a and 94a, respectively, allowing for an interlocking configuration individual camera controllers 91 thereby providing for a compact design. Each of the camera controllers 91 includes a connector, which may include a plurality of general-purpose input/output (GPIO) pins configured to be inserted into a corresponding connector on one of the interface boards 92, 93, 94.

The interface boards 92, 93, 94 are configured to power and provide structural support for the camera controllers 91 through the pin connections. Each of the interface boards 92, 93, 94 may include a 0.1 uF bypass capacitor for every individual camera controller 91, and two 3.5 mm pitch screw terminal blocks for 5V Power input and output. This particular design is modular and may be used to have a double-sided PCB, such as the interface board 93, and the same design can be used for the two single-sided PCBs, such as the interface boards 92 and 94.

Figure 8:
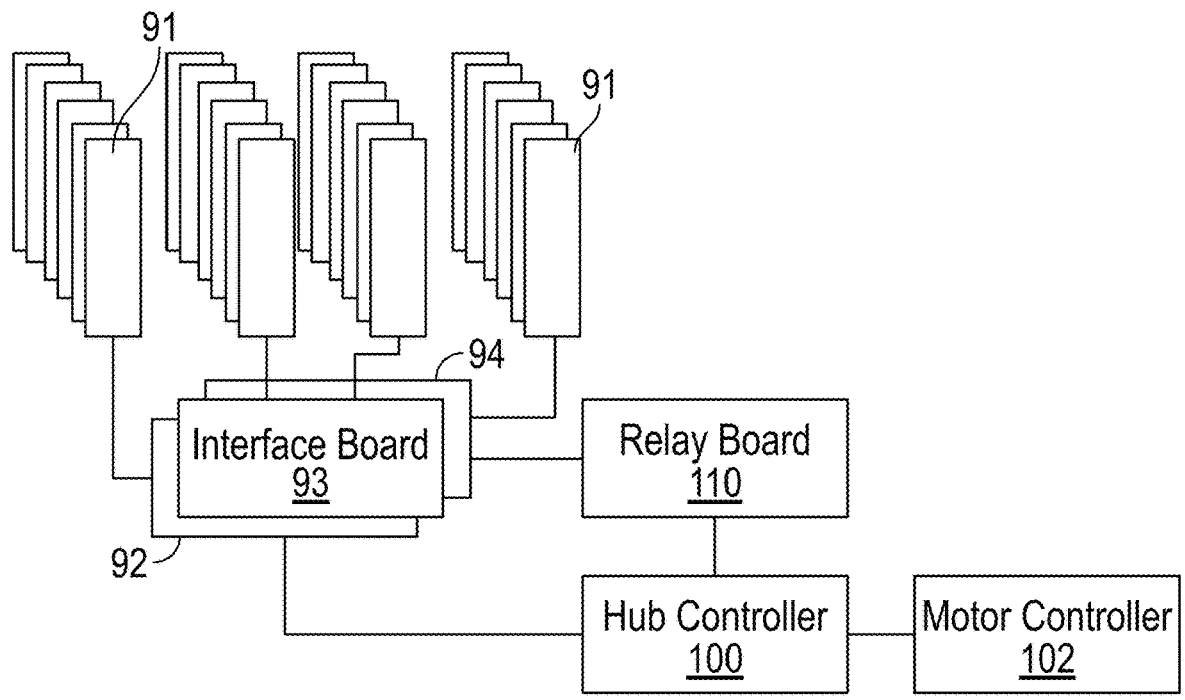
FIG. 8 is a schematic diagram of a computer architecture of the imaging device according to one embodiment of the present disclosure.

With reference to FIG. 8, the camera controllers 91 are coupled to a hub controller 100, which may be a Raspberry Pi 4, or any other suitable computing device. The hub controller 100 communicates with each of the camera controllers 91 using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The hub controller 100 is configured to command the cameras 44 to capture images, store captured images, process images, tag images, and the like. The hub controller 100 is also coupled to a motor controller 102, which may be an Arduino Uno and is configured to control movement of the actuators 16. In particular, the hub controller 100 is configured to output a movement command based on a desired distance movement and the motor controller 102 is configured to translate the movement command into a number of discrete steps for moving the actuators 16 to achieve the desired movement command.

Figure 9:
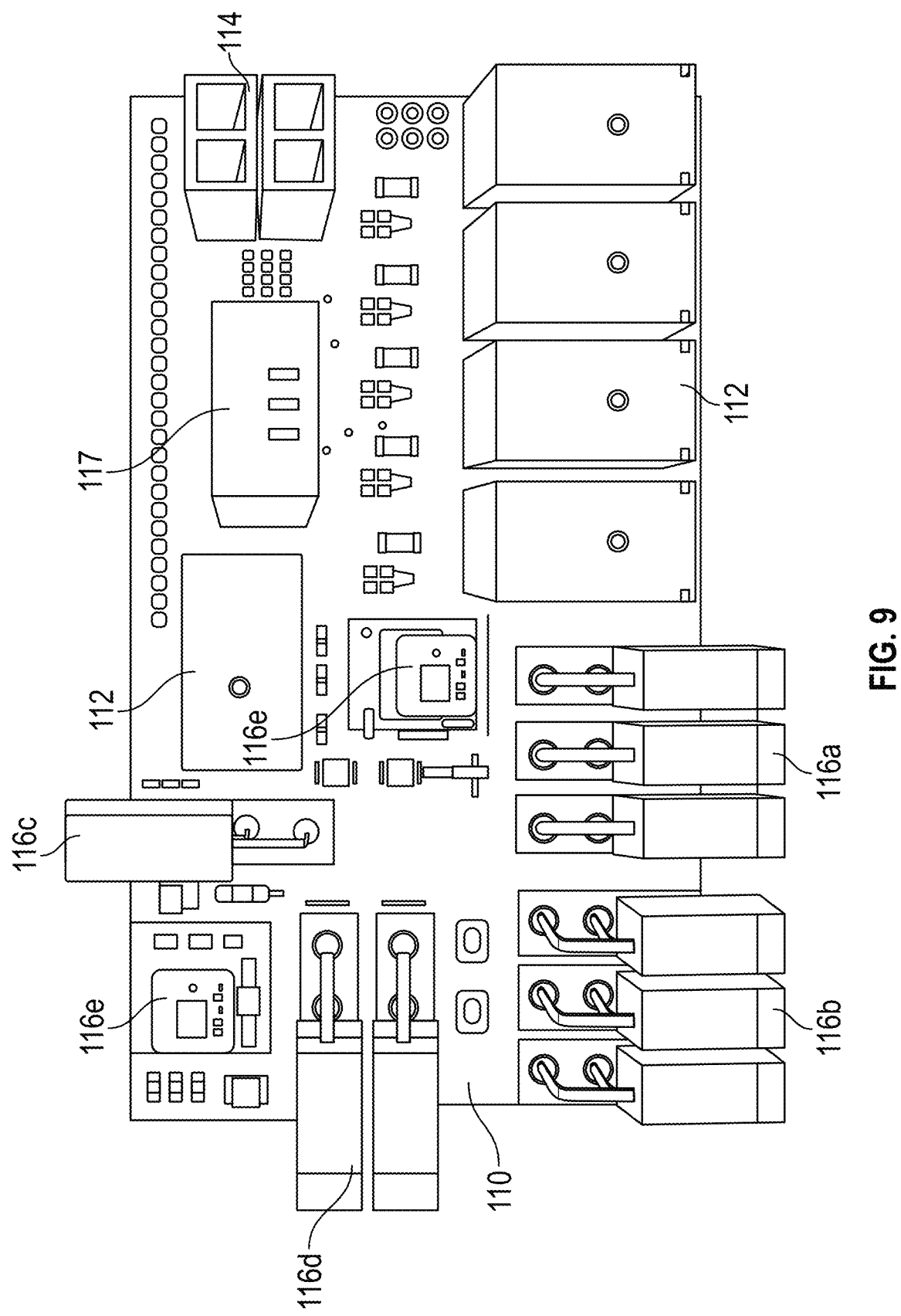
FIG. 9 is a plan view of an interface board of the imaging device according to one embodiment of the present disclosure.

With reference to FIGS. 8 and 9, the hub controller 100 is also coupled to a relay board 110 which is coupled to the motor controller 102. The relay board 110 may be a PCB and is configured to activate the first illumination assembly 50 and the second illumination assembly 80 individually as well as shut off power to the entire imaging device 10 in the event of an emergency.

The relay board 110 also includes relays 112 for controlling electrical output to the first illumination assembly 50 and the second illumination assembly 80. The relay board 110 also includes limit switch connectors 114 coupled to a lower limit switch 15 and an upper limit switch 17 (FIG. 2) engageable by the elevator platform 20 upon reaching lower and upper limits, respectively. The limit switches 15 and 17 may be InduSKY Micro Limit Switches with Momentary Roller Lever Arm AC 250V 5A SPDT 1NO 1NC Snap Action Micro Switches.

The relay board 110 further includes various power distribution components, including power distribution board connectors 116a for connecting to the interface boards 92, 93, 94, light board connectors 116b, motor power connectors 116c, power source connector (e.g., DC power supply) 116d, and voltage regulators 116e. The relay board 110 also includes a temperature and/or humidity sensor 117. Sensor data from the sensor 117 is provided to the hub controller 100. In the event humidity or temperature is outside operating limits, the hub controller 100 shuts down the imaging device 10, thereby protecting the imaging device 10 and the samples.

The sensor 117 may be used in conjunction with the fan 11 to control the temperature of the imaging device 10. In embodiments, the hub controller 100 may control the fan 11 (e.g., turning the fan 11 on or off, adjusting the speed, etc.) based on the temperature and/or humidity measurement data from the sensor 117. This is particularly useful when using the imaging device 10 with temperature sensitive samples and/or environment. In particular, the imaging device 10 may be used in temperature and/or humidity-controlled incubators. If the sensor 117 senses that temperature is excessive, then the hub controller 100 can shut down the imaging device 10 to prevent the incubator from overheating thereby preserving the cell culture samples "S" or increase the circulation of the fan 11.

The imaging process includes placing the cell culture plate 70 on the alignment platform 60. This may also include adjusting the position of the cell culture plate 70 on the alignment platform 60 along the x and y axes to align the well wells 72 with the imaging units 40. The hub controller 100 may then take images of the samples "S" held by the alignment platform 60 to confirm that the samples "S" are adequately illuminated and are in focus. The hub controller 100 may set light color and intensity of the first illumination assembly 50 and the second illumination assembly 80. The hub controller 100 also adjusts the vertical position of the elevator platform 20 to achieve desired focus of the images. Once these settings are finalized, the hub controller 100 may be programmed to set the duration of the longitudinal study, which may be from about 1 hour to about 30 weeks. The hub controller 100 also configures the frequency of the images being taken during the study period. After each set of pictures, the imaging unit returns to the lowest ("park") position, which is determined by activation of the lower limit switch 15 by the elevator platform 20.

Figure 10:
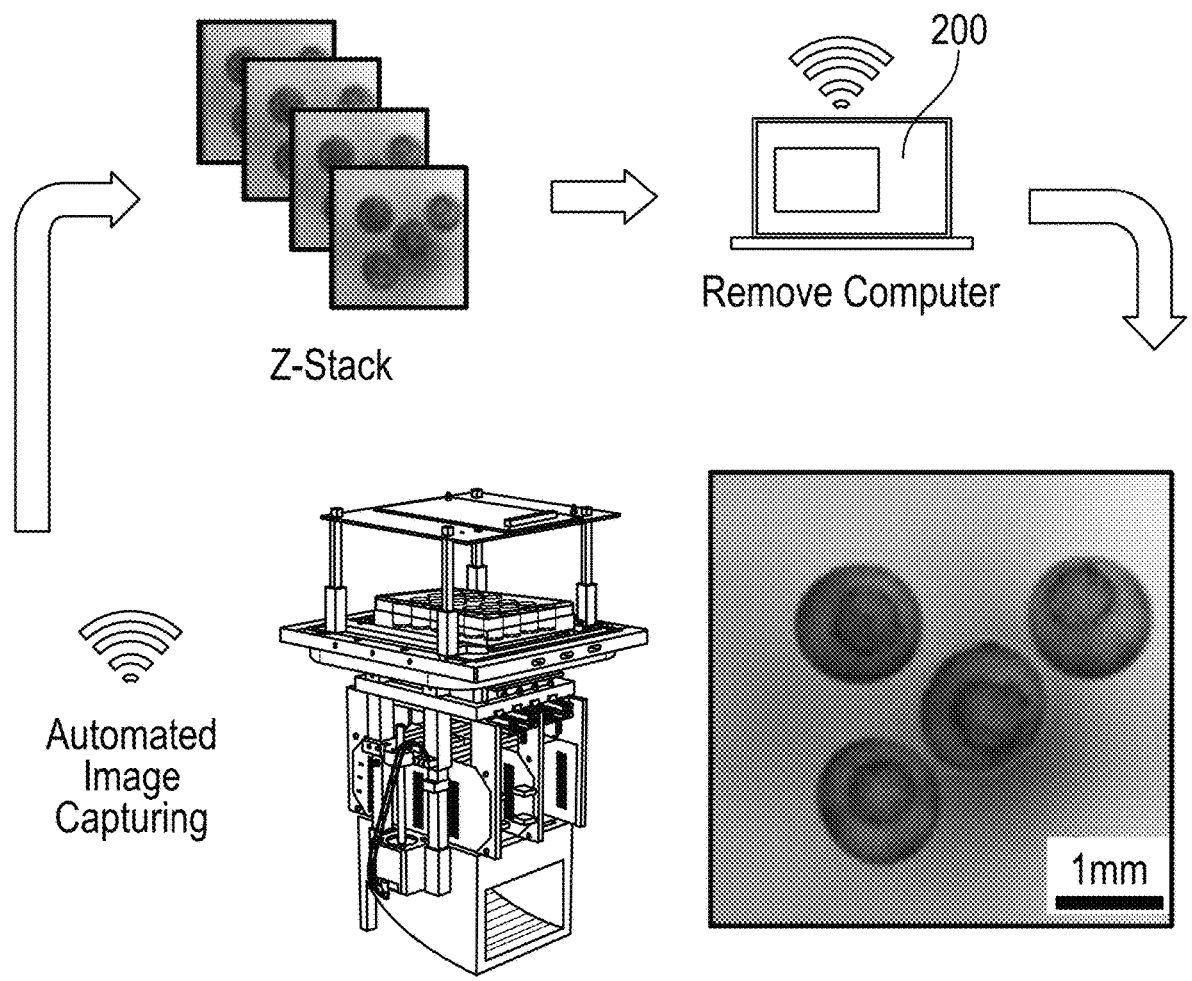
FIG. 10 is a schematic diagram of the imaging device communicating with a remote computer according to one embodiment of the present disclosure.
Figure 12:
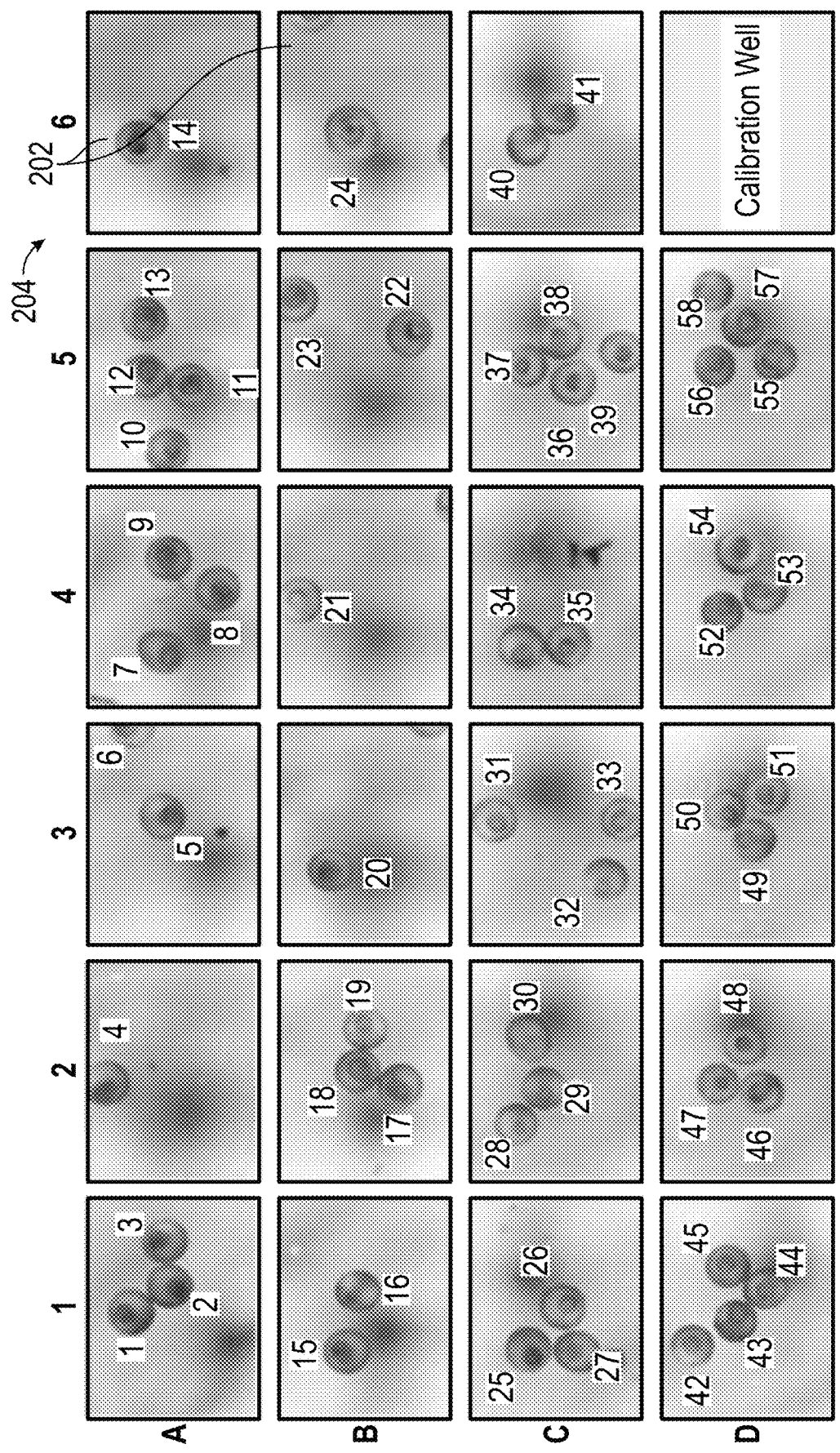
FIG. 12 are images of 23 samples held in the cell culture plate taken using the imaging device of FIG. 1 according to the present disclosure.

With reference to FIG. 10, the imaging device 10 is configured to communicate with a remote computer 200, which denotes any computer that is disposed outside the imaging device 10. As noted above, the hub controller 100 may include any suitable wireless or wired interface for connecting to the remote computer 200, which may be a laptop, a desktop, a server, or a virtualized computer. The images may then be transferred to the computer 200, where they can be viewed and/or processed with minimal intervention as shown in an exemplary image of FIG. 12. Image processing may include combining multiple images 202 into a single image 204 as shown in FIG. 12. Each of the well wells 72 is represented by a corresponding image 202, each of which was captured by an individual camera 44. The computer 200 may also include a display allowing for viewing of the images. In addition, the computer 200 may be used to adjust operating parameters of the imaging device 10 via the hub controller 100.

The computing devices (e.g., camera controllers 91, hub controller 100, computer 200 etc.) according to the present disclosure include a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

All of the electronic components of the imaging device 10 may be coated using an insulating and waterproof coating to waterproof the hardware so they could withstand the environment created by the incubator (e.g., high humidity and temperature). More specifically, the imaging device 10 may be operated in an incubator at a humidity of from about 75% to about 90% and a temperature of from about 35° C. to about 40° C., and in aspects of about 37° C.). This makes the imaging device 10 particularly useful when imaging inside incubators, which house mammalian tissue being studied. Due to the relatively small size, the imaging device 10 may be placed inside a tissue incubator having dimensions about 50 cm (width)×55 cm (depth)×70 cm (height).

The following Examples illustrate embodiments of the present disclosure. These Examples are intended to be illustrative only and are not intended to limit the scope of the present disclosure.

Example 1

This Example describes imaging of *Xenopus tropicalis* (frog) embryos using the imaging device according to the present disclosure.

Longitudinal live imaging capabilities of the imaging device according to the present disclosure were examined by imaging the development of frog embryos from the onset of gastrulation through organogenesis (FIGS. 12-15). The fertilization and development of *Xenopus* occurs entirely externally, which allows scientists to easily observe and manipulate the process. For decades, *Xenopus* have been heavily used in biology studies to model a variety of developmental processes and early onset of diseases, particularly those of the nervous system. While several species of *Xenopus* are used in different laboratories around the world, *Xenopus tropicalis* is one of the preferred species due to its diploid genomic composition and fast sexual maturation. Normal development and optimal husbandry of *Xenopus tropicalis* occurs at about 25° C. to about 27° C., closely approximating standard room temperature, which eliminates the need of special environmental control for most experiments.

Given these convenient experimental advantages and their large size, *Xenopus* embryos have been used extensively to understand the development of the vertebrate body plan, with particular success in elaborating the complex cellular rearrangements that occur during gastrulation and neural tube closure. These experiments rely on longitudinal imaging of developing embryos, often at single-embryo scale with dyes, fluorescent molecules, and computational tracking of single cells. These studies have elucidated key cellular mechanical properties and interactions critical to vertebrate development, often replayed and co-opted during tumorigenesis. There exists an opportunity to scale these experiments to have a higher throughput with the imaging device according to the present disclosure, as one could image hundreds of developing embryos simultaneously, rather than having to move the objective from embryo-to-embryo during development or repeating the experiment many times.

Figure 13:
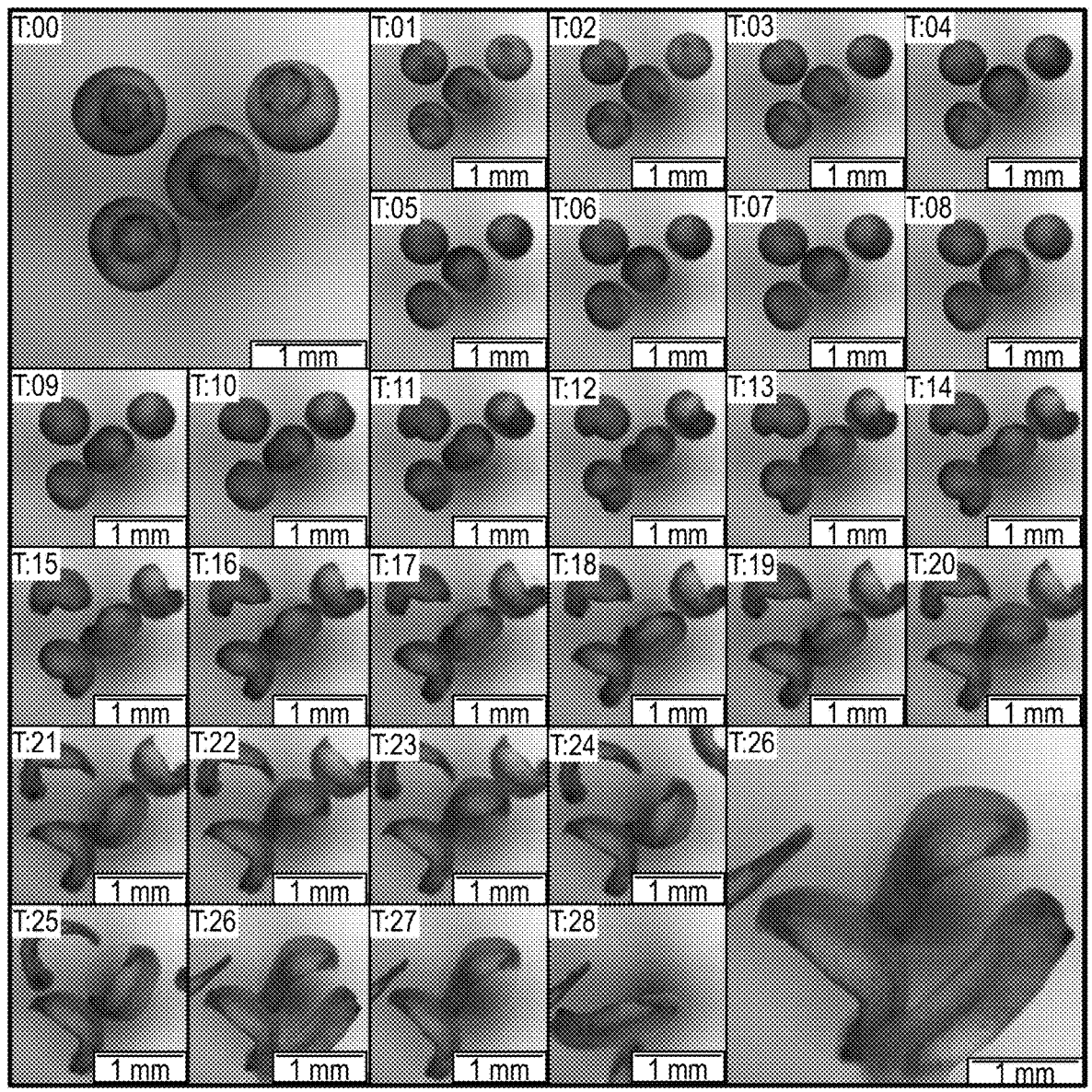
FIG. 13 are images of four frog embryos held in one well taken over approximately a 28-hour period taken approximately every hour using the imaging device of FIG. 1 according to the present disclosure.

Frog embryos were imaged over a 28-hour time period. Four embryos were placed in each of the 23 wells used in a 24-well plate, and an extra well in the bottom right corner was used for calibration (FIGS. 12 and 13). The embryos were grown in a saline solution and the experiment took place at room temperature. Imaging was performed hourly starting at gastrulation (FIGS. 14 and 15).

Figure 14:
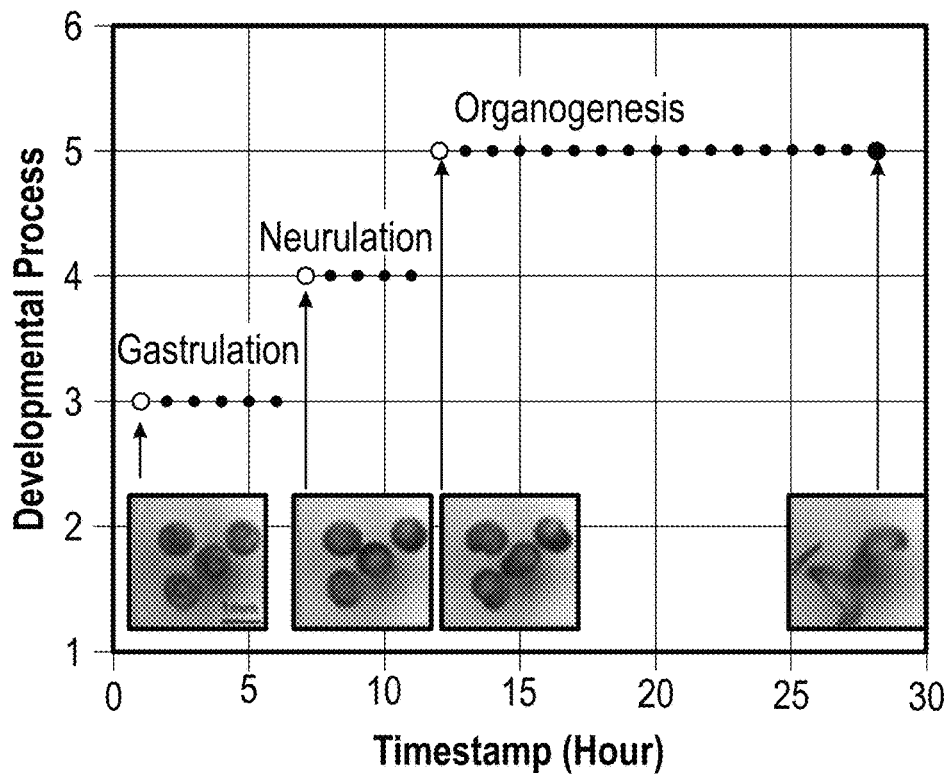
FIG. 14 is a plot of development of the frog embryos of FIG. 13, where each number on the y-axis represents the following developmental stages: 1—fertilization, 2—cleavage, 3—gastrulation, 4—neurulation, 5—organogenesis, 6—metamorphosis and x-axis represents a timestamp in hours.
Figure 15:
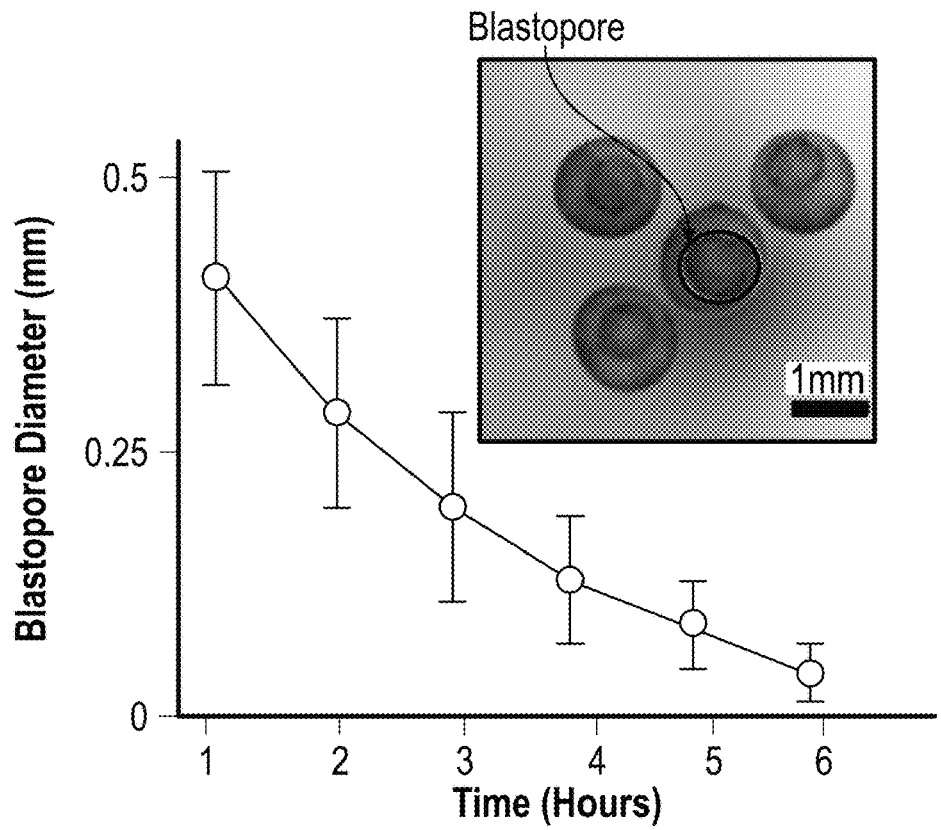
FIG. 15 is a plot of blastopore diameter over time as the blastopore transitions from gastrulation to neurulation.

Each image was visually inspected and mapped the embryos to the standard stages of frog development, categorizing their development in gastrulation, neurulation, and organogenesis (FIG. 14). Finally, the diameter of the blastopore of a subset of 27 embryos was measured as the embryos underwent gastrulation (FIG. 15). A progressive reduction of blastopore diameter was observed over a 6-hour time period, consistent with progression through gastrulation and the start of neurulation. This example demonstrated that the imaging device can be used for longitudinal sequential imaging and tracking of biological systems.

Example 2

This Example describes in-incubator imaging of human embryonic stem cells and brain organoids using the imaging device according to the present disclosure.

While many biological systems including zebrafish, planaria and frogs develop at room temperature and atmospheric gas concentrations, mammalian models require special conditions requiring an incubator enclosure. Mammalian models include 2D monolayer cell cultures, as well as 3D organoid models of development and organogenesis. They have been used to assess molecular features and effects of drugs for a variety of phenotypes including cell proliferation, morphology, and activity, among others.

Deploying electronics and 3D printed materials inside tissue culture incubators, which have increased humidity and temperature, presents some unique challenges. Increased temperature and humidity conditions can cause electronics to fail and cause certain plastics to off-gas toxins. Plastics can also be prone to deformation in these conditions. A common solution for protecting electronics and preventing off-gassing is to use inert protective coatings e.g., Parylene C. This requires expensive clean room equipment.

The imaging device according to the present disclosure is formed from 3D printed components from PLA, a non-toxic and biodegradable material. In order to prevent deformation, structural components were printed using 100% infill and reinforced vulnerable elements with aluminum MakerBeam profiles. All electronic components were coated with Corona Super Dope Coating from MG Chemicals to protect the electronics from the conditions, e.g., heat and humidity, of an incubator.

The functionality of the imaging device was tested inside a standard tissue culture incubator. FIG. 16A shows a thermal image obtained using an infrared camera of the imaging device is operated on a laboratory bench, which illustrates the heat generated by the imaging device. FIG. 16B shows a thermal image of the imaging device inside an incubator, which illustrates the heat surrounding the imaging device.

The imaging device obtained images of 2D-monolayers of human embryonic stem cells (hESCs) while being disposed in the incubator (FIG. 17). To demonstrate the capacity of the imaging device to perform longitudinal imaging across the z-axis, human cerebral cortex organoids embedded in MATRIGEL® were imaged (FIG. 18). Using the imaging device, the growth of the organoids was monitored, as well as the outgrowth of neuronal processes (FIGS. 19A and 19B). Tracking of individual cells within organoid outgrowths allowed for observation of their migration patterns and behavior (FIG. 19). Altogether, it was demonstrated that the imaging device according to the present disclosure is feasible for longitudinal imaging of mammalian cell and organoid models.

All hESC experiments used the H9 cell line (WiCell). hESCs were grown on vitronectin (Thermo Fisher Scientific, A14700) coated plates and cultured using StemFlex Medium (Thermo Fisher Scientific, A3349401). Passages were performed incubating the cells in 0.5 mM EDTA (Thermo Fisher Scientific, 15575020), in DPBS for 5 minutes.)

To generate cortical organoids, hESCs were first dissociated into single cells and re-aggregated them in Aggrewell 800 24-well plates (STEMcell Technologies) at a density of about 3,000,000 cells per well with 2 mL of Aggrewell Medium (STEMcell Technologies) supplemented with Rho Kinase Inhibitor (Y-27632, 10 µM, Tocris, 1254) (Day 0). The following day (Day 1), the aggregates were supplemented with WNT inhibitor (IWR1-ε, 3 µM, Cayman Chemical, 13659, Days 1-10) and TGF-βinhibitor (SB431542, Tocris, 1614, 5 µM, days 0-10). On Day 2, aggregates were transferred by pipetting out of the Aggrewell plate with a wide bore P1000 pipette tips onto a 37 µm filter and then transferred to ultra-low adhesion 6-well plates. Media was changed on Days 4, 8 and 10, by replacing 2 mL of conditioned media with fresh media. On Day 11 the medium was changed to Neuronal Differentiation Medium containing Eagle Medium: Nutrient Mixture F-12 with GlutaMAX supplement (DMEM/F12, Thermo Fisher Scientific, 10565018), 1×N-2 Supplement (Thermo Fisher Scientific, 17502048), 1× Chemically Defined Lipid Concentrate (Thermo Fisher Scientific, 11905031) and 100 U/mL Penicillin/Streptomycin supplemented with 0.1% recombinant human Fetal Growth Factor b (Alamone F-170) and 0.1% recombinant human Epidermal Growth Factor (R&D systems 236-EG). On Day 12, the organoids were transferred in 90 µL media to a custom glass-PDMS microfluidic chip for imaging/feeding containing 50 µL Matrigel hESC Qualif Matrix (BD 354277) bringing the total volume in the well to 120 µL. Partially embedding the organoid in Matrigel in this way led to 2D outgrowths on the surface of the Matrigel. Feeding occurred automatically every hour replacing 30 µL Neuronal Differentiation Medium.

Example 3

This Example describes imaging of planaria worms and zebrafish embryos using the imaging device according to the present disclosure.

The imaging device was also used to capture images of planaria worms. Planaria worms were purchased from Carolina Biological Supply Company (Catalog #132954). Planaria worms were grown in bottled water. Water was changed every other day. FIG. 21 shows images of the regeneration process of planaria worms taken at magnification scales of about 500 µm and 100 µm.

Zebrafish Fertilized zebrafish eggs were purchased from Carolina Biological Supply Company (Catalog #155591) and maintained in media containing 15 mM sodium chloride (Sigma-Aldrich, S9888), 0.5 mM potassium chloride (Sigma-Aldrich, P3911), 1 mM calcium chloride dihydrate (Sigma-Aldrich, 223506), 1 mM magnesium sulfate heptahydrate (Sigma-Aldrich, 1058822500), 150 µM potassium phosphate monobasic (Sigma-Aldrich, P5655), 50 sodium phosphate dibasic heptahydrate (Sigma-Aldrich, S9390), 0.7 mM sodium bicarbonate (Sigma-Aldrich, 55761) and 0.1% methylene blue (Sigma-Aldrich, M9140).

FIGS. 22 and 23 show images of zebrafish embryos from a longitudinal study. FIG. 22 shows a photograph of the embryos take at a magnification scale of 500 µm taken at 48 hours post fertilization. FIG. 23 shows images of zebrafish embryonic development at an oblong stage taken using the imaging device according to the present disclosure at magnification scales of about 500 µm and 100 µm.

It will be appreciated that of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims. Unless specifically recited in a claim, steps or components according to claims should not be implied or imported from the specification or any other claims as to any particular order, number, position, size, shape, angle, or material.

What is claimed is:

1. An imaging device comprising:
   an alignment platform configured to hold a cell culture plate including a plurality of wells;
   an imaging assembly disposed below the alignment platform, the imaging assembly including a plurality of imaging units, each of which is configured to image one well of the plurality of wells;
   a first illumination assembly disposed below the alignment platform and alongside the imaging assembly, the first illumination assembly configured to provide forward illumination of each well of the plurality of wells; and
   a second illumination assembly disposed above the alignment platform, the second illumination assembly configured to provide backlighting of each well of the plurality of wells.

2. The imaging device according to claim 1, further comprising:
   an elevator platform configured to support the imaging assembly and to move along a vertical axis transverse to a plane defined by the alignment platform.

3. The imaging device according to claim 2, further comprising:
   a base; and
   a plurality of columns extending vertically therefrom.

4. The imaging device according to claim 3, wherein the elevator platform is slidably coupled to the plurality of columns.

5. The imaging device according to claim 4, further comprising:
   at least one actuator configured to move the elevator platform along the vertical axis.

6. The imaging device according to claim 5, wherein the at least one actuator is an electric stepper motor.

7. The imaging device according to claim 5, further comprising:
   a motor controller configured to control the at least one actuator.

8. The imaging device according to claim 7, wherein each of the imaging units includes a camera body, a lens, and a camera.

9. The imaging device according to claim 8, further comprising a controller assembly including a plurality of camera controllers, each of which is coupled to one imaging unit of the plurality of imaging units.

10. The imaging device according to claim 9, wherein the controller assembly further includes at least one interface board configured to couple to the plurality of camera controllers.

11. The imaging device according to claim 10, further comprising:
    a hub controller configured to communicate with the plurality of camera controllers and the motor controller.

12. The imaging device according to claim 11, wherein the controller assembly, the hub controller, and the motor controller are coated by a waterproof coating.

13. The imaging device according to claim 12, wherein at least the alignment platform, the base, and the elevator platform are formed from polylactic acid.

14. The imaging device according to claim 12, wherein the imaging device is configured to operate in an incubator at a humidity of from about 75% to about 90% and a temperature of from about 35° C. to about 40° C.

* * * * *